(12) United States Patent
Bachar

(10) Patent No.: US 10,687,822 B2
(45) Date of Patent: Jun. 23, 2020

(54) THICKNESS-ADJUSTABLE HEMOSTATIC CLIPS, CLIP APPLIERS, AND APPLICATIONS THEREOF

(71) Applicant: CLIPTIP MEDICAL LTD, Yokneam Illit (IL)

(72) Inventor: Yehuda Bachar, Givaat Shmuel (IL)

( * ) Notice: Subject to any disclaimer, the term of this patent is extended or adjusted under 35 U.S.C. 154(b) by 222 days.

(21) Appl. No.: 15/877,621

(22) Filed: Jan. 23, 2018

(65) Prior Publication Data

US 2018/0146965 A1     May 31, 2018

Related U.S. Application Data

(63) Continuation-in-part of application No. PCT/IB2016/054408, filed on Jul. 24, 2016.

(60) Provisional application No. 62/196,323, filed on Jul. 24, 2015.

(51) Int. Cl.
| | | |
|---|---|---|
| *A61B 17/122* | (2006.01) | |
| *A61B 17/00* | (2006.01) | |
| *A61B 17/128* | (2006.01) | |
| *A61B 17/12* | (2006.01) | |

(52) U.S. Cl.
CPC .......... *A61B 17/122* (2013.01); *A61B 17/128* (2013.01); *A61B 2017/00862* (2013.01); *A61B 2017/12004* (2013.01)

(58) Field of Classification Search
CPC .............. A61B 17/122; A61B 17/1227; A61B 2017/00862; A61B 2017/12004; Y10T 24/44274
See application file for complete search history.

(56) References Cited

U.S. PATENT DOCUMENTS

| | | |
|---|---|---|
| 3,870,048 A | 3/1975 | Yoon |
| 4,226,239 A | 10/1980 | Polk et al. |
| 4,390,019 A | 6/1983 | LeVeen et al. |
| 4,425,915 A | 1/1984 | Ivanov |
| 4,763,398 A * | 8/1988 | Huizing ................. G02B 6/032 29/423 |

(Continued)

FOREIGN PATENT DOCUMENTS

| | | |
|---|---|---|
| EP | 2074954 A1 | 7/2009 |
| WO | 2004/066849 A1 | 8/2004 |
| WO | 2015/040621 A1 | 3/2015 |

*Primary Examiner* — Tuan V Nguyen

(57) ABSTRACT

Hemostatic clips, clip appliers, and applications thereof, for ligating bodily organs or tissues in a subject. Clip and clip appliers structurally conform to various thicknesses of bodily organs or tissues. The hemostatic clip includes opposing first and second clip arms connected at a shared elastic normally-opened joint portion. Clip arms include outer and inner members having tissue contacting surfaces, and gaps, for elastically deforming or/and shifting, to apply compression and clamping forces to bodily organ or tissue. Clip includes locking mechanism for locking clip arms together. Distal and proximal end portions may freely extend from a first arm joining portion. Clip includes interconnecting mechanism for sequentially chaining lengthwise multiple clips. Clip may include inner clip arm member with distal and proximal end portions freely extending from single arm joining portion. Also disclosed are clip appliers for deploying hemostatic clips, and methods employing hemostatic clips, for ligating bodily organs or tissue.

17 Claims, 17 Drawing Sheets

(56) References Cited

U.S. PATENT DOCUMENTS

| | | | |
|---|---|---|---|
| 4,800,879 A | 1/1989 | Golyakhovsky et al. | |
| 4,807,622 A | 2/1989 | Ohkaka et al. | |
| 5,046,611 A | 9/1991 | Oh | |
| 5,431,668 A | 7/1995 | Burbank, III et al. | |
| 5,462,555 A * | 10/1995 | Bolanos | A61B 17/122 606/120 |
| 5,725,542 A | 3/1998 | Yoon | |
| 5,846,255 A | 12/1998 | Casey | |
| 6,015,417 A | 1/2000 | Reynolds, Jr. | |
| 6,325,805 B1 | 12/2001 | Ogilvie et al. | |
| 6,610,073 B1 | 8/2003 | Levinson | |
| 6,679,894 B2 | 1/2004 | Damarati | |
| 7,001,399 B2 | 2/2006 | Damarati | |
| 7,001,412 B2 | 2/2006 | Gallagher et al. | |
| 7,052,504 B2 | 5/2006 | Hughett | |
| 7,094,245 B2 | 8/2006 | Adams et al. | |
| 7,211,092 B2 | 5/2007 | Hughett | |
| 7,316,696 B2 | 1/2008 | Wilson, Jr. et al. | |
| 7,494,461 B2 | 2/2009 | Wells et al. | |
| 7,585,304 B2 | 9/2009 | Hughett | |
| 7,879,052 B2 | 2/2011 | Adams et al. | |
| 8,062,311 B2 | 11/2011 | Litscher et al. | |
| 8,080,021 B2 | 12/2011 | Griego | |
| 8,088,061 B2 | 1/2012 | Wells et al. | |
| 8,133,240 B2 | 3/2012 | Damarati | |
| 8,444,660 B2 | 5/2013 | Adams et al. | |
| 8,663,247 B2 | 3/2014 | Menn et al. | |
| 8,685,048 B2 | 4/2014 | Adams et al. | |
| 8,709,027 B2 | 4/2014 | Adams et al. | |
| 8,915,837 B2 | 12/2014 | Wells et al. | |
| 8,936,610 B2 | 1/2015 | Damarati | |
| 9,044,239 B2 | 6/2015 | Griego | |
| 9,084,604 B2 | 7/2015 | Litscher et al. | |
| 9,204,883 B1 | 12/2015 | Riza et al. | |
| 9,271,731 B2 | 3/2016 | Adams et al. | |
| 9,332,988 B2 | 5/2016 | Adams et al. | |
| 2004/0066849 A1 | 4/2004 | Van Der Schaar | |
| 2004/0087987 A1 | 5/2004 | Rosenberg et al. | |
| 2005/0033333 A1 | 2/2005 | Smith et al. | |
| 2011/0009853 A1 | 1/2011 | Bertolero et al. | |
| 2012/0083803 A1 | 4/2012 | Patel | |
| 2014/0074131 A1 | 3/2014 | Armenteros et al. | |
| 2014/0243862 A1 | 8/2014 | Bagaoisan et al. | |
| 2015/0040621 A1 | 2/2015 | Myers et al. | |
| 2015/0048142 A1 | 2/2015 | Scheib et al. | |

* cited by examiner

100           FIG. 10

*{Ligating a bodily organ or tissue in a subject.}*

104

> Providing a distal-most hemostatic clip configured for surrounding the bodily organ or tissue. The distal-most hemostatic clip includes a first clip arm having a first clip arm distal end and a second clip arm having a second clip arm distal end, the second clip arm opposes and is pivotally linked to the first clip arm at a shared proximal end, and the second clip arm is movable relative to the first clip arm from a non-stressed fully opened clip configuration of the distal-most hemostatic clip.

108

> Providing a biasing mechanism between the first and second clip arms and allowing the biasing mechanism to occupy a space between the first and second clip arms and the bodily organ or tissue.

112

> Gradually closing the hemostatic clip over the bodily organ or tissue by forcibly decreasing distance between the first and second clip arm distal ends.

116

> Locking together the first and second clip arm distal ends to a closed clip height, via activating a locking mechanism.
>
> Gradually closing or/and locking effects the biasing mechanism into compressing and clamping the bodily organ or tissue, while being deformed at least partially into an outer periphery of the compressed and clamped bodily organ or tissue.

THICKNESS-ADJUSTABLE HEMOSTATIC CLIPS, CLIP APPLIERS, AND APPLICATIONS THEREOF

RELATED APPLICATIONS

This application is a Continuation-in-Part of International Patent Application No. PCT/IB2016/054408 filed 24 Jul. 2016, entitled "Thickness-Adjustable Hemostatic Clips, Clip Appliers, And Applications Thereof", which claims the benefit of priority under 35 USC 119(e) of U.S. Provisional Patent Application No. 62/196,323, filed Jul. 24, 2015, entitled "Thickness-Adjustable Hemostatic Clips, Clip Appliers, And Methods Of Use". The contents of the above applications are incorporated herein by reference in their entireties.

FIELD OF THE INVENTION

The present invention, in some embodiments thereof, relates to surgical type hemostatic clips, clip appliers, and applications thereof, suitable for ligating bodily organs or tissues in a subject.

BACKGROUND

During many surgical procedures blood vessels or other tubular structure have to be ligated and cut. Prior art includes various teachings about devices and techniques applicable for ligating bodily organs or tissues, such as blood vessels, among other possible bodily organs or tissues in a subject. Hemostatic clips are well known and commonly used in such teachings. Prior art also includes various teachings about using medical devices and procedures for applying surgical clips. For example, PCT Int'l. Appl. Pub. No. WO 2015/040621 A1, of same applicant/assignee as the present invention, discloses a laparoscopic clip applier which includes multiple clips housed in a rigid sleeve, where the arms of the clips are oriented lengthwise in the sleeve, and a deployment mechanism for deploying the clips from a distal end of the sleeve via a perforation made by a needle provided with the distal end of the sleeve.

In spite of extensive teachings in the field and art of the invention, and in view of significant limitations and potential problems associated with such teachings, there is an on-going need for developing and implementing new or/and improved hemostatic clips, clip appliers, and applications thereof, that are effective in overcoming such limitations or problems in medical procedures of, or involving, ligating bodily organs or tissues in a subject.

SUMMARY OF THE INVENTION

The present invention, in some embodiments thereof, relates to surgical type hemostatic clips, clip appliers, and applications thereof, for ligating bodily organs or tissues in a subject. In exemplary embodiments, the present invention relates to a thickness-adjustable hemostatic clip and clip applier. In exemplary embodiments, the clip applier is suitable for using the herein disclosed thickness-adjustable hemostatic clip. Exemplary embodiments of the present invention also relate to a method for ligating a bodily organ or tissue in a subject, for example, using the herein disclosed thickness-adjustable hemostatic clip and the clip applier.

In exemplary embodiments, the hemostatic clip of the invention includes pivotally linked first and second clip arm members, wherein at least one of the clip arm members has an outer rigid clip arm member and an inner clip arm member being resilient and elastic. In exemplary embodiments, the hemostatic clip further includes a locking mechanism configured for locking together the clip arms. In exemplary embodiments, the hemostatic clip shifts from a non-stressed fully opened configuration to a stressed locked configuration in which compressive forces are being applied to the bodily organ or tissue. In exemplary embodiments, the inner resilient clip arm member disposed within the herein disclosed hemostatic clip facilitates structural conformity of the clip to various thicknesses of bodily organs or tissues, and provides an efficient, long lasting, and safe tissue ligation. Such exemplary features, among others, of the herein disclosed invention may provide important advantages over currently known and used hemostatic clips, clip appliers, and applications thereof, for ligating bodily organs or tissues in a subject.

According to an aspect of some embodiments of the present invention, there is provided a thickness-adjustable hemostatic clip comprising: a first clip arm having a first clip arm distal end, and a second clip arm having a second clip arm distal end, the second clip arm opposes and is connected to the first clip arm at a shared proximal end configured as an elastic normally-opened joint portion, each one of the first and second clip arms includes an outer clip arm member connected to an inner clip arm member having a tissue contacting surface, and configured with a gap between the inner clip arm member and the outer clip arm member, such that the inner clip arm member elastically deforms or/and shifts towards a respective one of the outer clip arm member when the first and second clip arms are closed against, and mutually apply compression and clamping forces to, a bodily organ or tissue; and a locking mechanism configured for locking the first clip arm distal end to the second clip arm distal end; wherein a first one of the inner clip arm member is connected to a first one of the outer clip arm member, via at least one first arm joining portion, and includes both a distal end portion and a proximal end portion that freely extend from the at least one first arm joining portion.

According to some embodiments of the invention, the at least one first arm joining portion has a single first arm joining portion, wherein both the distal end portion and the proximal end portion of the first inner clip arm member freely extend from the single first arm joining portion.

According to some embodiments of the invention, the at least one of the distal end portion and the proximal end portion of the first inner clip arm member extends along a length greater than 3 mm from the single first arm joining portion.

According to some embodiments of the invention, the at least one first arm joining portion includes a proximal first arm joining portion and a distal first arm joining portion, wherein the distal end portion of the first inner clip arm member freely extends distally from the distal first arm joining portion, and the proximal end portion of the first inner clip arm member freely extends proximally from the proximal first arm joining portion.

According to some embodiments of the invention, the distal end portion of the first inner clip arm member extends along a length greater than 1 mm from the distal first arm joining portion, or/and the proximal end portion of the first inner clip arm member extends along a length greater than 0.5 mm from the proximal first arm joining portion.

According to some embodiments of the invention, a second one of the inner clip arm member is connected to a second one of the outer clip arm member, via at least one second arm joining portion distanced differently from the shared proximal end of the first and second clip arms relative to the at least one first arm joining portion.

According to some embodiments of the invention, the at least one second arm joining portion includes a distal-most second arm joining portion and a proximal-most second arm joining portion, wherein the at least one first arm joining portion is provided between the distal-most second arm joining portion and the proximal-most second arm joining portion.

According to some embodiments of the invention, the second inner clip arm member extends in full between the distal-most second arm joining portion and the proximal-most second arm joining portion.

According to some embodiments of the invention, the first inner clip arm member has an intermediate portion provided between the distal end portion and proximal end portion of the first inner clip arm member, wherein the first inner clip arm member is configured such that resistance to deformation or/and shift towards the first outer clip arm member is greater along the intermediate portion than along any of the distal end portion and the proximal end portion of the first inner clip arm member.

According to some embodiments of the invention, the first inner clip arm member has a first intermediate portion provided between the distal end portion and proximal end portion of the first inner clip arm member, wherein the first inner clip arm member is configured such that resistance to deformation or/and shift towards the first outer clip arm member is greater along the first intermediate portion than along any of the distal end portion and the proximal end portion of the first inner clip arm member; and wherein the second inner clip arm member has a second intermediate portion provided between a distal end portion and a proximal end portion of the second inner clip arm member, wherein the second inner clip arm member is configured such that resistance to deformation or/and shift towards the second outer clip arm member is smaller along the second intermediate portion than along any of the distal end portion and the proximal end portion of the second inner clip arm member.

According to some embodiments of the invention, the gap is sized for accommodating the inner clip arm member that conforms to the bodily organ or tissue and outwardly bends toward the respective outer clip arm member.

According to some embodiments of the invention, the first inner clip arm member is configured to apply a pressure of up to about 150 gr/mm$^2$ to the bodily organ or tissue.

According to some embodiments of the invention, the locking mechanism includes a hook with a hook flange, the hook extends from a hook leg originating from the distal first arm joining portion and extending distally across entire length of the distal end portion of the first inner clip arm member.

According to some embodiments of the invention, the locking mechanism further includes a niche with a cam surface in a form of a distal extension of second clip arm distal to second inner clip arm member, wherein the hook flange is configured to slidably engage along and beyond the cam surface, then fasten to niche, when the first and second clip arms shift from an opened clip configuration to a locked clip configuration.

According to some embodiments of the invention, the hook leg portion is curved towards first inner clip arm member until a hook apex provided distally and adjacent to distal end portion, wherein the distal end portion of the first inner clip arm member is configured to flex towards the hook leg portion, when pressed against the bodily organ or a tissue towards engaging with second clip arm, thereby supporting a length of the hook leg portion up to a point located adjacently and proximally to the hook apex.

According to some embodiments of the invention, the first and second clip arms, and the locking mechanism, are integrally structured and manufactured from a single piece of material.

According to some embodiments of the invention, the hemostatic further comprises an interconnecting mechanism configured for sequentially chaining lengthwise, one after another, a plurality of the hemostatic clip, wherein the shared proximal end includes a tail coupler connectable to a head coupler provided at the second clip arm distal end.

According to an additional aspect of some embodiments of the present invention, there is provided a thickness-adjustable hemostatic clip comprising: a first clip arm having a first clip arm distal end; a second clip arm having a second clip arm distal end, the second clip arm opposes and is pivotally linked to the first clip arm at a shared proximal end, and the second clip arm is movable relative to the first clip arm from a non-stressed fully opened clip configuration wherein the first clip arm distal end is distanced from the second clip arm distal end by a predetermined distance, to a stressed locked clip configuration wherein the first clip arm distal end is in proximity with or contacts the second clip arm distal end; wherein at least one of the first and second clip arms includes an outer rigid clip arm member connected to an inner resilient elastic clip arm member having a tissue contacting surface; and a locking mechanism configured for applying resistive force to the first clip arm distal end or to the second clip arm distal end, thereby locking the first clip arm distal end to the second clip arm distal end during the locked clip configuration, so as to prevent self-opening of the hemostatic clip.

According to such an embodiment of the hemostatic clip, the first and second clip arms, when deployed in the locked clip configuration, are configured for applying compression and clamping forces to a bodily organ or tissue via the inner resilient elastic clip arm member while allowing the inner resilient elastic clip arm member to compress or shift laterally towards a respective the outer rigid clip arm member, such that in response to the deployment, the first and second clip arms are conformable to a compressed and clamped shape of the bodily organ or tissue while exerting clamping forces thereto.

According to some embodiments of the invention, the outer rigid arm member is configured to prevent deformation thereof in response to elastic deformation of the inner resilient elastic clip arm member and to limit expansion of the inner resilient elastic clip arm member.

According to some embodiments of the invention, the outer rigid clip arm member joins the inner resilient elastic clip arm member at two separate joining portions, whereby the outer and inner clip arm members enclose a gap extending between the joining portions, the gap separates a roof surface of the outer rigid clip arm member away from a roof-contact surface of the inner resilient elastic clip arm member. According to some embodiments of the invention, the inner resilient elastic clip arm member is configured for laterally bending or protruding towards an opposing inner arm member. According to some embodiments of the invention, the gap is sized for accommodating the inner resilient elastic clip arm member conforming to tissue and outwardly bending toward the outer rigid clip arm member, until at least part of the roof-contact surface contacts at least part of the roof surface.

According to some embodiments of the invention, a first and a second of the at least one inner resilient elastic clip arm member are configured to apply a pressure of up to about 150 gr/mm² to the bodily organ or tissue, wherein the applied pressure is constant or linearly rising in relation to thickness of tissue located between the first and second inner resilient elastic clip arms, under the compression and clamping forces applied to the bodily organ or tissue before being restricted in expansion by each the outer rigid clip arm member.

According to some embodiments of the invention, a first and a second of the at least one inner resilient elastic clip arm members are configured to apply a compressive pressure above 150 gr/mm² to the bodily organ or tissue, wherein the applied pressure rapidly rises in relation to thickness of compressed material of the first and second inner resilient elastic clip arm members or of compressed tissue therebetween when the first and second inner resilient elastic clip arm members are in close contact with respective the outer rigid clip arm members.

According to some embodiments of the invention, a first and a second of the at least one inner resilient elastic clip arm members are configured to apply a compressive pressure of at least 5 gr/mm² when separated by a distance of at least 0.1 mm therebetween.

According to some embodiments of the invention, a first and a second of the at least one inner resilient elastic clip arm members are configured to apply a compressive pressure in a range of between about 10 gr/mm² and about 150 gr/mm² when separated by a distance in a range of between about 0.2 mm and about 0.8 mm therebetween.

According to some embodiments of the invention, a first and a second of the at least one inner resilient elastic clip arm members are configured for approaching each other and reducing a gap therebetween, while continuously conforming to the compressed shape of the bodily organ or tissue clamped therebetween in response to gradual shrinking of the bodily organ or tissue during or/and after necrosis thereof.

According to some embodiments of the invention, each inner resilient elastic clip arm member is configured for evenly distributing pressure exerted on the bodily organ or tissue in contact therewith in response to the deployment.

According to some embodiments of the invention, the locking mechanism comprises a hook having a first end connected to the first clip arm distal end. According to some embodiments of the invention, the hook comprises a second end having a hook flange with a follower surface, wherein the hook first end is adapted for slidably engaging a cam surface provided on the second clip arm distal end, in response to the first and second clip arms moving from the opened clip configuration to the locked clip configuration. According to some embodiments of the invention, the first and second clip arms shift into the locked clip configuration following the hook flange reaching and fitting into a niche positioned beyond the cam surface. According to some embodiments of the invention, the first and second clip arms, and the locking mechanism, are integrally structured and manufactured from a single piece of material.

According to some embodiments of the invention, the hemostatic clip further comprises an interconnecting mechanism configured for sequentially chaining lengthwise, one after another, a plurality of the hemostatic clip, wherein a hemostatic clip proximal end includes a tail coupler connectable to a head coupler provided at the first clip arm distal end or at the second clip arm distal end.

According to some embodiments of the invention, opposing two of the inner resilient elastic clip arm members are configured to apply a compressive pressure of at least 5 gr/mm² when separated by a distance of at least 0.1 mm therebetween. According to some embodiments of the invention, opposing two of the inner resilient elastic clip arm members are configured to apply a compressive pressure in a range of between about 10 gr/mm² and about 150 gr/mm² when separated by a distance in a range of between about 0.2 mm and about 0.8 mm therebetween. According to some embodiments of the invention, opposing two of the inner resilient elastic clip arm members are configured for approaching each other and reducing a gap therebetween while being continuously conformable to the compressed and clamped shape of the bodily organ or tissue clamped therebetween, in response to gradual shrinking of the bodily organ or tissue during or/and after necrosis thereof.

According to some embodiments of the invention, the inner resilient elastic clip arm member is configured for evenly distributing pressure exerted on periphery of the bodily organ or tissue in contact therewith in response to the deployment and compressing of a ligated bodily organ or tissue.

According to another aspect of some embodiments of the present invention, there is provided a clip applier for deploying hemostatic clips onto a bodily organ or tissue in a subject, the clip applier comprising: at least one thickness-adjustable hemostatic clip, including a distal-most thickness-adjustable hemostatic clip, comprised of: a first clip arm having a first clip arm distal end; a second clip arm having a second clip arm distal end, movable relative to the first clip arm from a non-stressed fully opened clip configuration of the distal-most hemostatic clip; and a locking mechanism configured for locking the first clip arm distal end to the second clip arm distal end, so as to prevent self-opening of the hemostatic clip; wherein at least one of the first and second clip arms includes an outer rigid clip arm member connected to an inner resilient elastic clip arm member having a tissue contacting surface, such that when deployed, the clip arm members are configured for applying clamping forces to a bodily organ or tissue via each inner resilient elastic clip arm member while allowing each inner resilient elastic clip arm member to compress or shift laterally towards a respective rigid outer clip arm member, such that in response to the deployment, the first and second clip arms conform to a compressed shape of the bodily organ or tissue; and a trigger mechanism including an inner sleeve and configured for sliding and advancing the inner sleeve from a retracted position that uncovers the distal-most hemostatic clip, to a protruding position that covers the distal-most hemostatic clip.

According to such an embodiment of the hemostatic clip applier, the inner sleeve, when advanced to the protruding position over the first and second clip arms of the distal-most hemostatic clip effects moving of the first and second clip arms to approach each other so as to self-lock the first and second clip arms by the locking mechanism of the distal-most hemostatic clip.

According to some embodiments of the invention, the distal-most hemostatic clip includes a first and a second of the at least one inner resilient elastic clip arm member, and a first and a second of the respective outer rigid clip arm member, wherein the inner sleeve includes two opposing tracks sized and shaped for accommodating corresponding runner surfaces of the respective outer rigid clip arm members in contact therewith, when in the protruding position, thereby confining and defining a maximal achievable gap between the first and second inner resilient elastic clip arm members for the deployment, when the first and second inner resilient elastic clip arm members contact the respective outer rigid clip arm members.

According to some embodiments of the invention, the distal-most hemostatic clip includes a first and a second of the at least one inner resilient elastic clip arm member, and wherein the hemostatic clip and the trigger mechanism are shaped and sized for forcing the first and second inner resilient elastic clip arm members to align in a predetermined formation in which distance between the first and second clip arm distal ends is equal to or less than a predetermined opening that allows shifting of the first and second clip arms into the locked clip configuration upon the inner sleeve reaching the protruding position. According to some embodiments of the invention, the opposing tracks are parallel to each other.

According to another aspect of some embodiments of the present invention, there is provided a clip applier for ligating a bodily organ or tissue in a subject, the clip applier comprising: at least one hemostatic clip, including a distal-most hemostatic clip comprised of: a first clip arm having a first clip arm distal end; a second clip arm having a second clip arm distal end, the second clip arm opposes and is pivotally linked to the first clip arm at a shared proximal end, and the second clip arm is movable relative to the first clip arm from a non-stressed fully opened clip configuration of the distal-most hemostatic clip; and a locking mechanism configured to lock together the first and second clip arm distal ends to a closed clip height being smaller than an opened clip height of a non-stressed fully opened clip configuration; and a clip pressing mechanism, including a sliding press, and configured for selectively moving the sliding press across the distal-most hemostatic clip between a fully retracted position proximal to the distal-most hemostatic clip, and a fully protruded position across the distal-most hemostatic clip, so as to limit the opened clip height of the distal-most hemostatic clip to a maximal opened clip height being equal to or less than the closed clip height.

According to such an embodiment of the hemostatic clip applier, when the clip applier is deployed, shifting the sliding press from a retracted position to the fully protruded position effects gradual closing of the hemostatic clip by decreasing distance between the first and second clip arm distal ends, at least until reaching the closed-clip height, so as to activate the locking mechanism to lock together the first and second clip arm distal ends at the closed clip height, for facilitating ligation of the bodily organ or tissue.

According to some embodiments of the invention, the sliding press includes a tubular member. According to some embodiments of the invention, the tubular member is in a form of an inner sleeve axially slidable in a lumen of an outer sleeve, wherein the inner sleeve is configured to be withdrawn proximal to distal end of the outer sleeve when the clip pressing mechanism is in the fully retracted position, and is configured to protrude at least partially distal to the outer sleeve distal end when the clip pressing mechanism is in the protruding position. According to some embodiments of the invention, the outer sleeve is in a form of a needle or/and the outer sleeve distal end includes a sharp edge. According to some embodiments of the invention, the tubular member includes an inner lumen dimensioned for limiting opening of the distal-most hemostatic clip to the maximal opened clip height.

According to some embodiments of the invention, the clip applier is configured such that retracting the sliding press to the fully retracted position when the first and second clip arm distal ends are locked together into a locked configuration via the locking mechanism, effects release and ejection of the distal-most hemostatic clip therefrom.

According to some embodiments of the invention, the clip applier further comprises a biasing mechanism provided between the first and second clip arms, and configured for compressing a ligated bodily organ or tissue while being deformed to outer periphery of the compressed ligated bodily organ or tissue. According to some embodiments of the invention, the biasing mechanism is part of the distal-most hemostatic clip. According to some embodiments of the invention, the biasing mechanism comprises an inner clip arm member, wherein each of the first and second clip arms includes an outer clip arm member connected to a corresponding the inner clip arm member, wherein each inner clip arm member has a tissue contacting surface being conformable or/and displaceable in response to the compressing of the ligated bodily organ or tissue.

According to some embodiments of the invention, the distal-most hemostatic clip, when in the locked configuration, is configured for applying compression and clamping forces to the bodily organ or tissue via each the inner clip arm member while allowing the tissue contacting surface to at least partially conform to the outer clip arm member or/and to a compressed and clamped shape of the bodily organ or tissue, in response to ligating of the bodily organ or tissue, wherein each the outer arm clip member is configured for preventing deformation thereof in response to the conformity of the inner arm clip member tissue contacting surface.

According to some embodiments of the invention, the inner clip arm member is compactable or/and bendable towards the outer clip arm member in response to the conformity. According to some embodiments of the invention, the outer clip arm member joins the inner clip arm member at two separate joining portions, whereby the outer and inner clip arm members enclose a gap extending between the joining portions, the gap separates a roof surface of the outer clip arm member away from a roof-contact surface of the inner clip arm member. According to some embodiments of the invention, the inner clip arm member is configured for laterally bending or protruding towards an opposing inner clip arm member. According to some embodiments of the invention, the gap is sized for accommodating the inner clip arm member conforming to tissue and outwardly bending toward the outer clip arm member, until at least part of the roof-contact surface contacts at least part of the roof surface.

According to some embodiments of the invention, a first and a second of the at least one inner clip arm member are configured to apply a pressure of up to about 150 gr/mm$^2$ to the bodily organ or tissue, wherein the applied pressure is constant or linearly rises in relation to thickness of tissue located between the first and second inner clip arms, under the compression and clamping forces applied to the bodily organ or tissue before being restricted in expansion by each the outer clip arm member.

According to some embodiments of the invention, a first and a second of the at least one inner clip arm members are configured to apply a compressive pressure above 150 gr/mm$^2$ to the bodily organ or tissue, wherein the applied pressure rapidly rises in relation to thickness of compressed bodily tissue or organ of the first and second inner clip arm members or of compressed tissue therebetween when the first and second inner clip arm members are in close contact with respective the outer clip arm members.

According to some embodiments of the invention, a first and a second of the at least one inner clip arm members are configured to apply a compressive pressure of at least 5 gr/mm$^2$ when separated by a distance of at least 0.1 mm therebetween. According to some embodiments of the invention, a first and a second of the at least one inner clip arm members are configured to apply a compressive pressure in a range of between about 10 gr/mm$^2$ and about 150 gr/mm$^2$ when separated by a distance in a range of between about 0.2 mm and about 0.8 mm therebetween. According to some embodiments of the invention, a first and a second of the at least one inner clip arm members are configured for approaching each other and reducing a gap therebetween while continuously conforming to the compressing of the bodily organ or tissue clamped therebetween in response to gradual shrinking of the bodily organ or tissue during or/and after necrosis thereof.

According to some embodiments of the invention, each inner clip arm member is resilient elastic and configured for resisting shaping thereof. According to some embodiments of the invention, each inner clip arm member is configured for evenly distributing pressure exerted on periphery of the bodily organ or tissue in contact therewith in response to the compressing of the ligated bodily organ or tissue.

According to another aspect of some embodiments of the present invention, there is provided a method for ligating a bodily organ or tissue in a subject, the method comprising: providing a distal-most hemostatic clip configured for surrounding the bodily organ or tissue, wherein the distal-most hemostatic clip comprises a first clip arm having a first clip arm distal end and a second clip arm having a second clip arm distal end, the second clip arm opposes and is pivotally linked to the first clip arm at a shared proximal end, and the second clip arm is movable relative to the first clip arm from a non-stressed fully opened clip configuration of the distal-most hemostatic clip; providing a biasing mechanism between the first and second clip arms and allowing the biasing mechanism to occupy a space between the first and second clip arms and the bodily organ or tissue; gradually closing the hemostatic clip over the bodily organ or tissue by forcibly decreasing distance between the first and second clip arm distal ends; and locking together the first and second clip arm distal ends to a closed clip height, via activating a locking mechanism; wherein the gradually closing or/and the locking effects the biasing mechanism into compressing and clamping the bodily organ or tissue, while being deformed at least partially into an outer periphery of the compressed and clamped bodily organ or tissue.

According to some embodiments of the invention, the providing includes providing the distal-most hemostatic clip in a clip applier, the clip applier comprises a clip pressing mechanism, including a sliding press, and configured for selectively moving the sliding press across the distal-most hemostatic clip between a fully retracted position proximal to the distal-most hemostatic clip, and a fully protruded position across the distal-most hemostatic clip, so as to limit an opened clip height of the distal-most hemostatic clip to a maximal opened clip height.

According to some embodiments of the invention, the method further comprises releasing and ejecting the distal-most hemostatic clip from the clip applier. According to some embodiments of the invention, the releasing and ejecting includes retracting the sliding press to the fully retracted position after the first and second clip arm distal ends are locked together via the locking mechanism. According to some embodiments of the invention, the moving of the sliding press to the fully protruded position over the hemostatic clip initiates the activating of the locking mechanism.

According to some embodiments of the invention, the gradually closing the hemostatic clip includes the moving of the sliding press from the retracted position to the fully protruded position. According to some embodiments of the invention, the maximal opened clip height is equal to or less than the closed clip height.

According to some embodiments of the invention, each of the first and second clip arms comprises an outer arm member, wherein the biasing mechanism includes at least one resilient elastic inner clip arm member connected to a corresponding the inner clip arm member, wherein each inner clip arm member has a tissue contacting surface being conformable or/and displaceable in response to compressing of a ligated bodily organ or tissue.

According to some embodiments of the invention, the gradually closing or/and the locking includes applying compression forces to the bodily organ or tissue via the at least one inner clip arm member while allowing the tissue contacting surface to at least partially conform to the outer clip arm member or/and to a compressed and clamped shape of the bodily organ or tissue.

According to some embodiments of the invention, the inner clip arm member is configured for being compactable or/and bendable towards the outer clip arm member in response to the conformity, or/and the outer clip arm member connected thereto is configured for preventing deformation thereof in response to conformity of the inner clip arm member. According to some embodiments of the invention, the outer clip arm member joins the inner clip arm member at two separate joining portions, whereby the outer and inner clip arm members enclose a gap extending between the joining portions, the gap separates a roof surface of the outer clip arm member away from a roof-contact surface of the inner clip arm member.

According to some embodiments of the invention, the compressing and clamping the bodily organ or tissue while being deformed to the outer periphery thereof includes allowing the inner clip arm member to laterally bend or protrude towards a second opposing inner clip arm member. According to some embodiments of the invention, the gap is sized for accommodating the inner clip arm member conforming to tissue outwardly bending toward the outer clip arm member, until at least part of the roof-contact surface contacts at least part of the roof surface.

According to some embodiments of the invention, the compressing and clamping the bodily organ or tissue includes applying a constant or linearly increasing compressive pressure of up to about 150 gr/mm$^2$ to the compressed and clamped bodily organ or tissue, wherein the applied pressure is constant or linearly rises in relation to thickness of tissue located between the first and second clip arms. According to some embodiments of the invention, the compressing and clamping the bodily organ or tissue includes applying a compressive pressure above 150 gr/mm$^2$ to the bodily organ or tissue following full conformity of shape thereof to the corresponding outer clip arm member, wherein the applied pressure is constant or linearly rises in relation to thickness of tissue located between the first and second clip arms.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 10 is a flow diagram of an exemplary embodiment of a method of ligating a bodily organ or tissue in a subject, using the herein disclosed hemostatic clip applier and hemostatic clip, in accordance with some embodiments of the invention;

DETAILED DESCRIPTION OF SPECIFIC EMBODIMENTS OF THE INVENTION

Figure 1A:
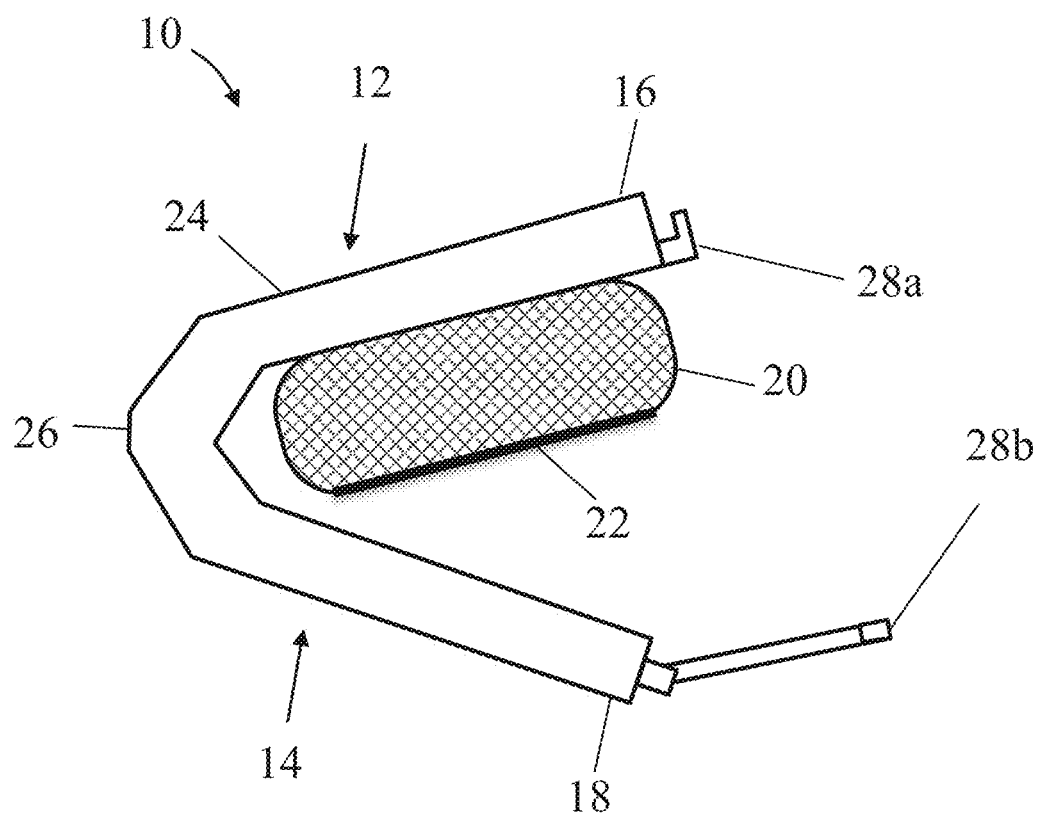
FIGS. 1A-1D are schematic side views showing a hemostatic clip, in a non-stressed fully opened configuration (FIG. 1A), a closed and unlocked without a bodily organ or tissue configuration (FIG. 1B), a locked configuration without a bodily organ or tissue (FIG. 1C), and a stressed locked configuration (FIG. 1D), in accordance with some embodiments of the invention.

The present invention, in some embodiments thereof, relates to surgical type hemostatic clips, clip appliers, and applications thereof, for ligating bodily organs or tissues in a subject. In exemplary embodiments, the present invention relates to a thickness-adjustable hemostatic clip and clip applier. In exemplary embodiments, the clip applier is suitable for using the herein disclosed thickness-adjustable hemostatic clip. Exemplary embodiments of the present invention also relate to a method for ligating a bodily organ or tissue in a subject, for example, using the herein disclosed thickness-adjustable hemostatic clip and the clip applier.

In exemplary embodiments, the hemostatic clip of the invention includes pivotally linked first and second clip arm members, wherein at least one of the clip arm members has an outer rigid clip arm member and an inner clip arm member being resilient and elastic. In exemplary embodiments, the hemostatic clip further includes a locking mechanism configured for locking together the clip arms. In exemplary embodiments, the hemostatic clip shifts from a non-stressed fully opened configuration to a stressed locked configuration in which compressive forces are being applied to the bodily organ or tissue. In exemplary embodiments, the inner resilient clip arm member disposed within the herein disclosed hemostatic clip facilitates structural conformity of the clip to various thicknesses of bodily organs or tissues, and provides an efficient, long lasting, and safe tissue ligation. Such exemplary features, among others, of the herein disclosed invention may provide important advantages over currently known and used hemostatic clips, clip appliers, and applications thereof, for ligating bodily organs or tissues in a subject.

Hemostatic clips are effective tools for ligating a blood vessel, or, other bodily organ or tissue. However, currently used clips or/and clip appliers are frequently associated with failure to effectively ligate a blood vessel, thereby causing continued bleeding in a subject. The inventors observed that a significant limitation and problem associated with currently employed hemostatic clips is non-conformity of the structural configuration of the clips to various thicknesses of blood vessels. Such structural non-conformity is associated with blood vessels being either too thin or too thick for the hemostatic clip to effect full ligation of the blood vessel. For example, structural non-conformity of a hemostatic clip to a relatively thin blood vessel results in a gap being formed between two arms of a closed hemostatic clip. Consequently, the clip may become loose, thereby, not effectively ligating the blood vessel or the tubular structure, and may even slide off the cut end of the blood vessel. Alternatively, for example, applying a clip to a relatively thick tissue, such as a larger vessel or other tubular structure in the subject's body, may result in excessive pressure being exerted upon the vessel wall, possibly tearing the vessel, causing premature necrosis and bleeding, or/and preventing closure of the clip on the vessel or tubular structure altogether.

While some prior art hemostatic clips may be associated with such complications caused by ineffective tissue ligation due to incompatibility to tissue thickness, the present invention aims to overcome this limitation and provides a hemostatic clip and clip applier which are thickness adjustable, hence facilitate efficient ligations to various tissue thicknesses.

It is understood that the invention is not limited to the particular methodology, protocols, and anatomy, etc., described herein, as these may vary as the skilled artisan will recognize. It is also to be understood that the terminology used herein is used for the purpose of describing particular embodiments only, and is not intended to limit the scope of the invention. The following exemplary embodiments may be described in the context of exemplary bodily organ or tissue ligating procedures for ease of description and understanding. However, the invention is not limited to the specifically described devices and methods, and may be adapted to various clinical applications without departing from the overall scope of the invention.

An aspect of some embodiments of the present invention relates to a thickness-adjustable hemostatic clip including: a first clip arm having a first clip arm distal end and a second clip arm having a second clip arm distal end. The second clip arm opposes and is pivotally linked to the first clip arm at a shared proximal end, and the second clip arm is movable relative to the first clip arm from a non-stressed fully opened clip configuration to a stressed locked clip configuration, wherein in the non-stressed fully opened clip configuration the first clip arm distal end is distanced from the second clip arm distal end by a predetermined distance, and in the stressed locked clip configuration the first clip arm distal end is in proximity with or contacts the second clip arm distal end. At least one of the first and second clip arms includes an outer rigid clip arm member connected to an inner resilient elastic clip arm member having a tissue contacting surface. The hemostatic clip further includes a locking mechanism configured for applying resistive force to the first clip arm distal end or to the second clip arm distal end, thereby locking the first clip arm distal end to the second clip arm distal end during the locked configuration, so as to prevent self-opening of the hemostatic clip. The first and second clip arms, when deployed in the locked clip configuration, while ligating a bodily organ or tissue, are configured for applying compression and clamping forces to the bodily organ or tissue via at least one of the inner resilient elastic clip arm member while allowing at least a portion of the inner resilient elastic clip arm member to compress or shift laterally towards a respective outer rigid clip arm member, such that in response to the clip deployment and ligating, the first and second clip arms are conformable to a compressed and clamped shape of the bodily organ or tissue.

Referring now to the drawings, FIGS. 1A-1D are schematic side views showing a hemostatic clip according to some embodiments of the invention. Simplified illustrations of the hemostatic clip 10 of the invention for ligating the bodily organ or tissue which is bodily organ or tissue thickness-adjustable is shown. The hemostatic clip 10 includes a first clip arm 12 and a second clip arm 14 linked at a shared proximal end 26. The first clip arm 12 includes a first clip arm distal end 16 and the second clip arm 14 includes a second clip arm distal end 18. At least one of clip arms 12 and 14 includes an outer rigid clip arm member 24. At least one of clip arms 12 and 14 include an inner resilient elastic clip arm member 20. In some embodiments, at least one of clip arms 12 and 14 includes an outer rigid clip arm member 24 connected to an inner resilient elastic clip arm member 20. In some embodiments, each of clip arms 12 and 14 includes an outer rigid clip arm member 24 connected to an inner resilient elastic clip arm member 20. Inner resilient elastic clip arm member 20 may include a tissue contacting surface 22. Hemostatic clip 10 further includes a locking mechanism 28 including locking units 28a and 28b.

Hemostatic clip 10 may have a length within a range of between about 2 mm to about 50 mm.

The diameter of hemostatic clip may be less than about 7 mm, less than about 5 mm, less than about 4 mm, less than about 3 mm, less than about 2 mm or less than about 1 mm. Each possibility represents another exemplary embodiment of the invention.

Inner resilient elastic clip arm member 20 is configured such that various ranges of tissues thicknesses may be efficiently ligated by the hemostatic clip of the invention. In some embodiments, the hemostatic clip 10 is suitable for ligating a bodily tissue or organ having a thickness within a range of between about 0.1 mm and about 10 mm, which may be compressible up to a compressed thickness within a range of between about 0.1 mm and 1 mm, where applicable.

Hemostatic clip 10 may exhibit a configuration selected from the group consisting of: non-stressed fully opened, closed and unlocked configuration, and stressed locked.

The following examples describe in details hemostatic clip 10 in the various configurations.

Referring to FIG. 1A, clip 10 is shown in a non-stressed fully opened configuration. In the fully opened configuration, first clip arm distal end 16 is distanced from second clip arm distal end 18 by a predetermined distance. In some embodiments, the term "predetermined distance" is interchangeable with the term "closed clip height". In some embodiments, the predetermined distance is the maximal distance or height displayed between first clip arm distal end 16 and second clip arm distal end 18.

In some embodiments, the predetermined distance may display a height/distance value within the range of between about 0.3 mm to about 5 mm.

Figure 1B:
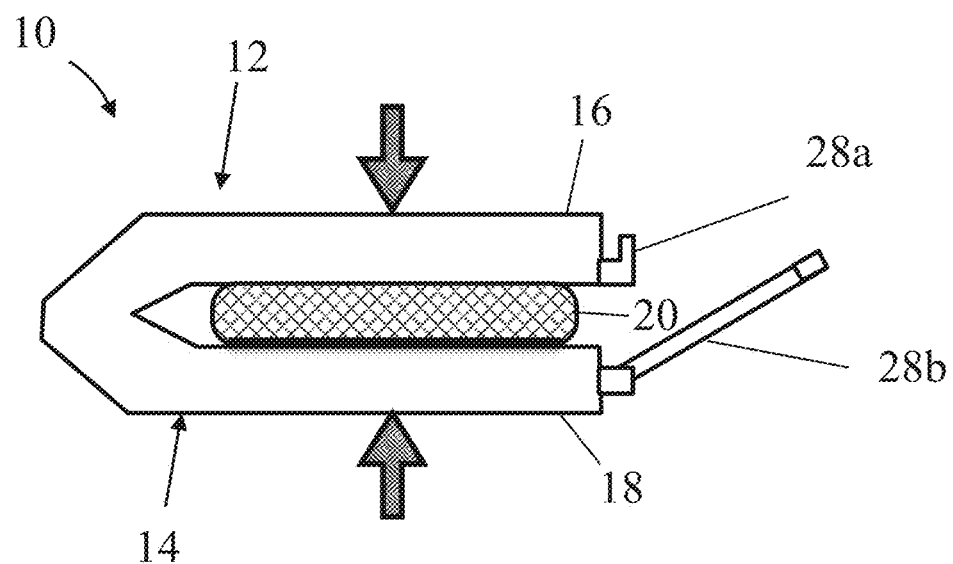

Referring to FIG. 1B, clip 10 is shown in a closed and unlocked without a bodily tissue or organ ligated thereby. Compressive forces (shown by arrows) are operated on hemostatic clip 10 when confined within restricting boundaries, such as imposed by a sleeve of a clip applier, for example. The clip applier and the compressive forces operated on the hemostatic clip will be described in more details below. In the closed and unlocked without a bodily organ and tissue configuration, clip arm distal end 16 and clip arm distal end 18 are in close proximity and may or may not contact each other.

Figure 1C:
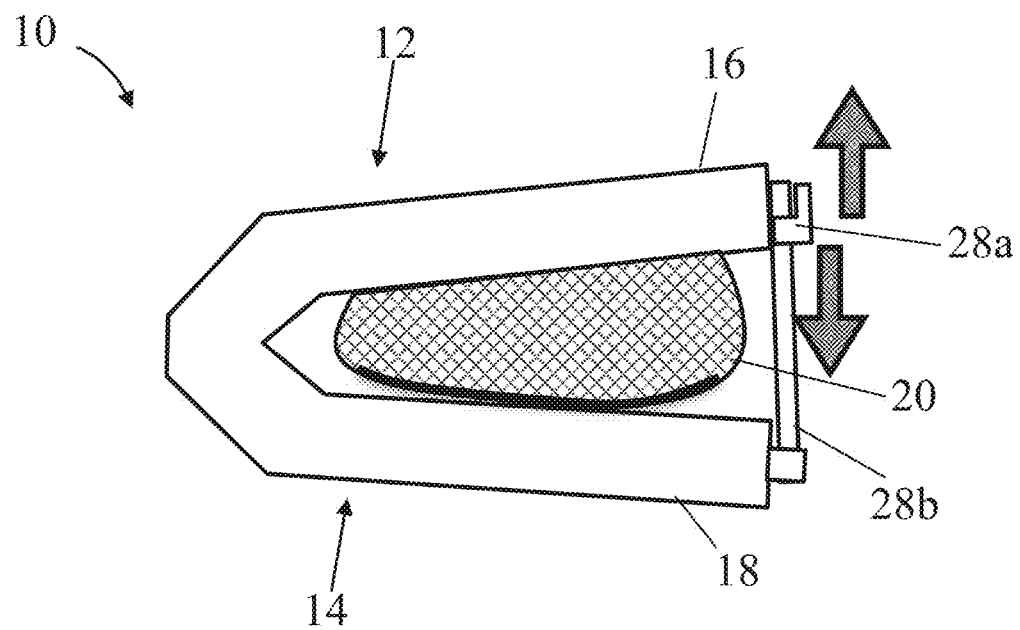

Referring to FIG. 1C, clip 10 is shown in a locked configuration. Locking mechanism 28 is locked and resistive forces (shown by arrows) are operated on the hemostatic clip. Clip arm distal end 16 and clip arm distal end 18 are in close proximity and may or may not contact each other.

Figure 1D:
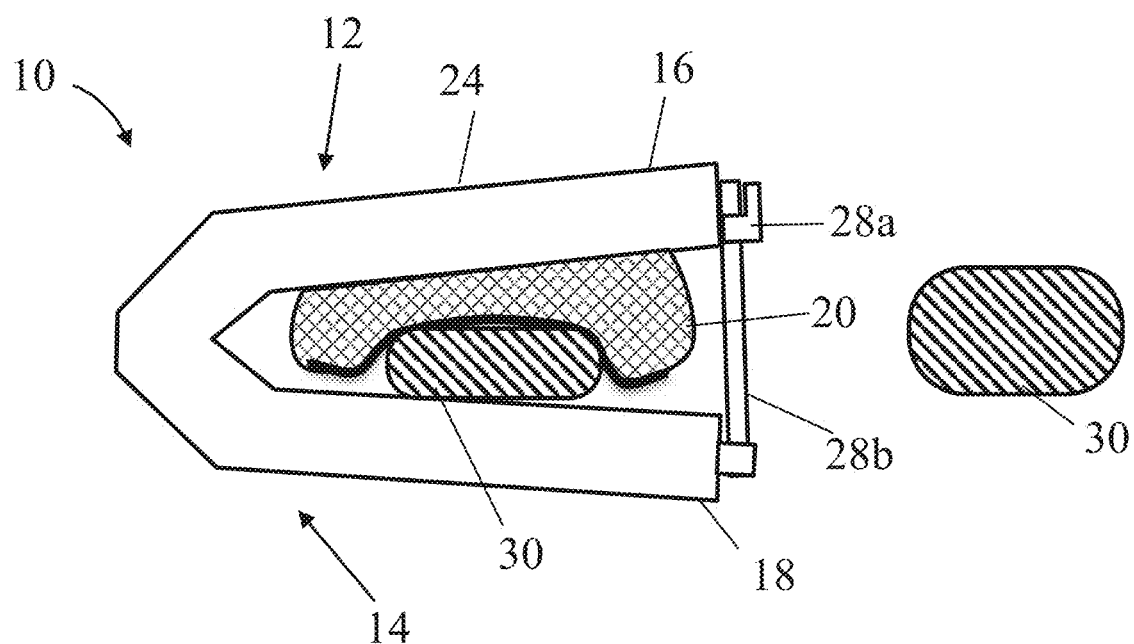

Referring to FIG. 1D, clip 10 is shown in a stressed locked configuration. In this configuration first and second clip arms 12 and 14 apply compression and clamping forces towards a bodily organ or tissue 30 via at least one of inner resilient elastic clip arm member 20. The at least one of the inner resilient elastic clip arm member 20 conforms to the outer compressed shape, curvature or/and dimensions (e.g. thickness and/or shape) of bodily organ or tissue 30. For example, in response to ligating a bodily organ or tissue, at least a portion of the inner resilient elastic clip arm member 20 compresses laterally towards a respective outer rigid clip arm member 24. Optionally, additionally or alternatively, inner resilient elastic clip arm member 20 laterally bends or protrudes towards an opposite inner resilient elastic clip arm member or clip arm. In response to ligating a bodily organ or tissue, outer rigid clip arm member 24 prevents deformation of clip arms 12 and 14. Locking mechanism 28 is closed and thereby opening of the hemostatic clip by resistive forces operated on the hemostatic clip is prevented. Clip arm distal end 16 and clip arm distal end 18 are in close proximity and may or may contact each other.

According to some embodiments, clip arms 12 and 14 may be in close proximity in one of the following hemostatic clip 10 configurations: closed and unlocked configuration (no bodily tissue or organ being ligated), and stressed locked configuration (with a bodily tissue or organ being ligated). According to some embodiment, clip arm distal ends 16 and 18 may be in close proximity in one of the following hemostatic clip 10 configurations: closed and unlocked configuration (no tissue being ligated), and stressed locked configuration.

The term "close proximity" means that a space is present between first clip arm 12 and second clip arm 14. In some embodiment, the space diameter may depend on the clip configuration and/or the bodily tissue or organ dimensions (i.e. shape and thickness).

Ligating a bodily tissue or organ includes transition of the hemostatic clip from a non-stressed fully opened configuration (FIG. 1A) to a stressed locked configuration (FIG. 1D). Accordingly, and during ligating a bodily tissue or organ, the second clip arm 14 is movable relative to the first clip arm 12. By "movable relative to" it is meant that either one or both first clip arm 12 and second clip arm 14 are movable towards each other.

Ligating a bodily tissue or organ includes gradually closing hemostatic clip 10 over bodily organ or tissue 30, by forcibly decreasing distance between clip arm 12 and clip arm 14, or between clip arm distal end 16 and clip arm distal end 18. Ligating a bodily tissue or organ further includes locking together by locking mechanism 28 first and second clip arm distal ends 16 and 18.

Inner resilient elastic clip arm member 20 is configured to conform to various thicknesses of bodily organs or tissues. By "conform" or "conformity" it is meant that inner resilient elastic clip arm member 20 is shaped in response to ligating a bodily tissue or organ. In some embodiments, inner resilient elastic clip arm member 20 is bendable.

In some embodiments, inner resilient elastic clip arm member 20 is made of an elastic material. In some embodiments, inner resilient elastic clip arm member 20 is made of a biocompatible material.

Exemplary suitable elastic materials are, but not limited to, elastic type polymers, elastic metals, elastic metal alloys (e.g. nickel-titanium, stainless steel, cobalt chrome, Titanium), or a combination thereof.

During ligating a bodily organ or tissue, inner resilient elastic clip arm member 20 continuously conforms, optionally only partly, to the clamped bodily organ or tissue, while exerting compressing/clasping affecting pressure thereto, until full bodily organ or tissue ligation is accomplished. In some embodiments, inner resilient elastic clip arm member 20 evenly distributes pressure exerted on the bodily organ or tissue being ligated. In some embodiments, when only one of clip arms 12 and 14 includes an inner resilient elastic clip arm member 20, the inner resilient elastic clip arm distributes, optionally evenly, pressure exerted on the bodily organ or tissue between the inner resilient elastic clip arm member 20 and an opposite clip arm member.

In some embodiments, inner resilient clip arm member 20 includes a tissue contacting surface 22. The tissue contacting surface 22 may be made from a material similar or not to the material inner resilient clip arm member 20 is made of. In some embodiments, inner resilient clip arm member 20 facilitates bodily organ or tissue grasping. In some embodiments, tissue contacting surface 22 may be disposed with serrations, teeth or rough surface.

Outer rigid clip arm member 24 is configured to support any deformation of inner resilient member 20 in response to bodily organ or tissue ligation. Outer rigid clip arm member 24 is further configured to limit expansion of inner resilient elastic clip arm member 20.

In accordance with those embodiments, outer rigid clip arm member 24 may be made of any suitable material as long as deformation in response to ligating a bodily tissue or organ of outer rigid clip arm member 24 is prevented. Some exemplary suitable materials are, but not limited to: Ni—Ti alloy, Titanium, or a combination thereof.

Shared proximal end 26 facilitates connection between clip arms 12 and 14. Shared proximal end 26 may be shaped and of any suitable structure that connects clip arms 12 and 14. For example, shared proximal end 26 may connect clip arms 12 and 14 by a hinge which may be integrally formed with at least one of clip arms 12 and 14 (an exemplary shared proximal end is described below with reference to FIG. 4).

Clip arms 12 and 14 are configured to apply compression and/or clamping forces towards the bodily organ or tissue via at least one of inner resilient elastic clip arm members 20 in response to ligating a bodily organ or tissue. In some embodiments, the pressure applied is constant. In some embodiments, the pressure applied linearly rises in relation to the stage of the bodily organ or tissue ligation. In some embodiments, the pressure applied depends on the bodily organ or tissue thickness. Optionally, during the course of ligation and prior to becoming restricted in expansion by outer rigid clip arm member 24, at least one of inner resilient elastic clip arm members 20 applies a pressure of up to about 300 $gr/mm^2$, or optionally, up to about 150 $gr/mm^2$, to the bodily organ or tissue.

Further optionally, when in close contact with outer rigid clip arm member 24, the at least one of inner resilient elastic clip arm members 20 applies a pressure of above 150 $gr/mm^2$ or of above 300 $gr/mm^2$ on the bodily organ or tissue.

Further optionally, the at least one inner resilient elastic clip arm members 20 applies a compressive pressure of at least 5 $gr/mm^2$, at least 10 $gr/mm^2$ or at least 15 $gr/mm^2$ when a distance of at least 0.1 mm separates between a first and a second inner resilient elastic clip arm members 20, or between a first inner resilient elastic clip arm member 20 and an opposite clip arm member. In some embodiments, the at least one inner resilient elastic clip arm member 20 applies a compressive pressure in a range of between about 10 $gr/mm^2$ to about 150 $gr/mm^2$, when a distance in a range of between about 0.2 mm and about 0.8 mm separates between a first and a second inner resilient elastic clip arm member 20, or between a first inner resilient elastic clip arm member 20 and an opposite clip arm member.

Locking mechanism 28 includes locking units 28a and 28b, each is optionally provided at a different clip arm. Locking mechanism 28 is configured for applying resistive forces to at least one of first clip arm distal end 16 and second clip arm distal end 18, thereby locking the first clip arm distal end 16 to the second clip arm distal end 18. Further, locking mechanism 28 is configured to prevent self-opening of the hemostatic clip. Locking units 28a and 28b may each extend from first clip arm distal end 16 and first clip arm distal end 18, respectively. Locking units 28a and 28b may each be integrally structured and manufactured from a single piece of material of first clip arm 12 and first clip arm 14.

Figure 2A:
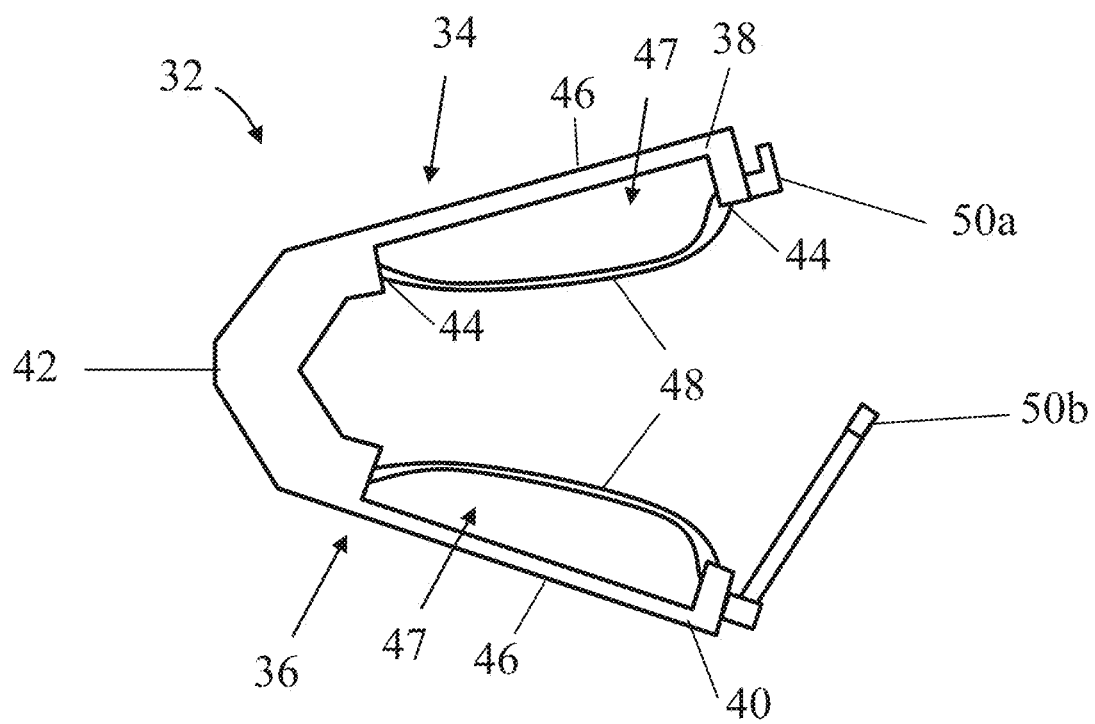
FIGS. 2A-2B are schematic side views of an exemplary hemostatic clip, in a non-stressed fully opened configuration (FIG. 2A), and a locked configuration without a bodily organ or tissue (FIG. 2B), in accordance with some embodiments of the invention.
Figure 2B:
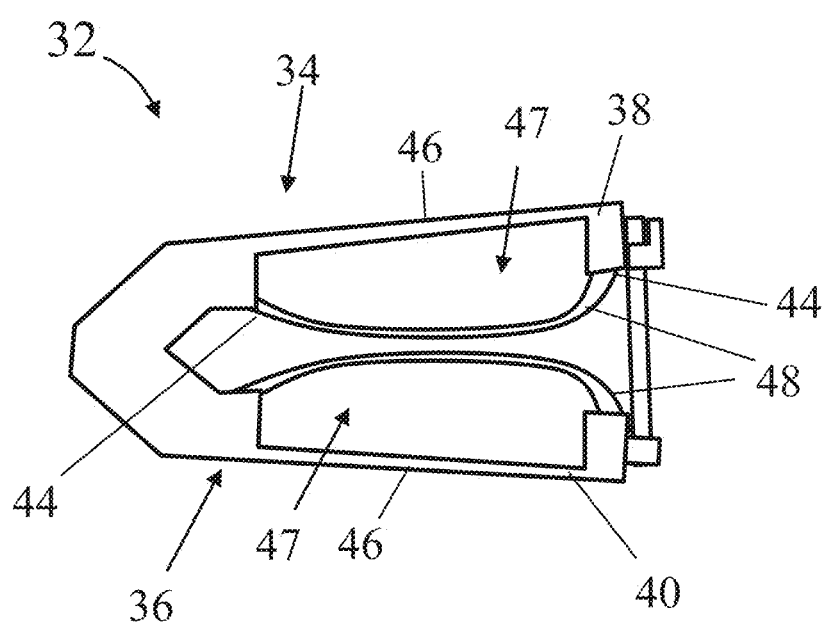

Reference is now made to FIGS. 2A-2B, which illustrate a schematic side view of an exemplary hemostatic clip 32 operative with some embodiments of the invention. Hemostatic clip 32 is an exemplary hemostatic clip 10 which includes inner resilient elastic clip arm member 48 (correspond to inner resilient elastic clip arm member 20 of hemostatic clip 10) at each of first clip arm 34 and second clip arm 36 (correspond respectively to first clip arm 12 and second clip arm 14 of hemostatic clip 10). Further, hemostatic clip 10 demonstrates joint portion 44 which joins together inner resilient elastic clip arm member 48 with outer rigid clip arm member 46 (corresponds to outer rigid clip arm 24 of hemostatic clip 10). Similar to hemostatic clip 10, first clip arm 34 and second clip arm 36 of hemostatic clip 32 are linked at a shared proximal end 42 (corresponds to shared proximal end 26 of hemostatic clip 10) and include a first clip arm distal end 38 (corresponds to first clip arm distal end 16 of hemostatic clip 10) and a second clip arm distal end 40 (corresponds to second clip arm distal end 18 of hemostatic clip 10), respectively. Further similar to hemostatic clip 10, locking mechanism 50 locks together first and second clip arm members 34 and 36. Inner resilient elastic clip arm member 48 may include a tissue contacting surface (not shown, corresponds to tissue contacting surface 22 of hemostatic clip 10).

Joint portion 44 may be integral to at least one of clip arm members 34 and 36. Joint portion 44 may be a separate element connecting clip arm members 34 and 36. Joint portion 44 may be made from a material similar to rigid clip arm member 46. Alternatively, joint portion 44 may be made from the same material similar to inner resilient elastic clip arm member 48, including but not limited to at least one of Ni—Ti alloy, Titanium, or other elastic biocompatible metal or polymer.

Outer rigid clip arm member 46 and inner resilient elastic clip arm member 48 enclose a gap 47 that separates an inner surface of the outer rigid clip arm member 46 from a roof-contact surface of the inner resilient elastic clip arm member 48. In some embodiments, and depending on the dimensions of the bodily organ or tissue (i.e. shape and/or thickness) to be ligated and/or configuration of the hemostatic clip (i.e. non-stressed fully opened, closed and unlocked without a bodily organ or tissue, and stressed locked), gap 47, per each clip arm, is about 0.8 mm or less in maximal height, optionally about 0.5 mm or less, or optionally about 0.4 mm.

Inner resilient elastic clip arm members 48 present on each of clip arm 34 and clip arm 36 may have a space therebetween or may contact each other. The space depends on the clip's configuration (i.e. non-stressed fully opened, closed and unlocked without a bodily organ or tissue, or stressed locked) and/or the bodily tissue or organ dimensions. For example, when hemostatic clip 32 is closed and unlocked without a bodily organ or tissue or stressed locked the space diameter may be about 0.1 mm or less.

Referring to FIG. 2A, side view of hemostatic clip 32 in a non-stressed fully opened configuration is shown. Referring to FIG. 2B, side view of hemostatic clip 32 in a stressed locked configuration is shown.

Figure 3A:
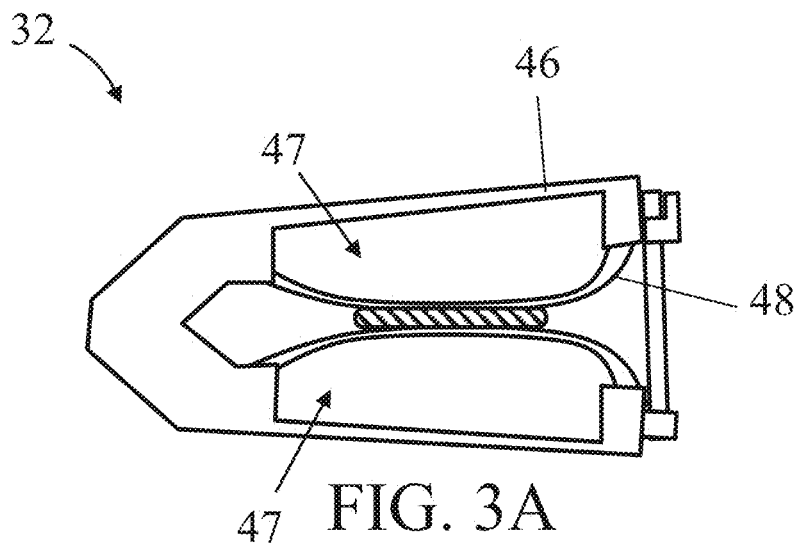
FIGS. 3A-3C is a schematic side view of an exemplary hemostatic clip which is thickness adjustable and conforms various tissue thicknesses upon ligating a bodily tissue or organ, in accordance with some embodiments of the invention.
Figure 3B:
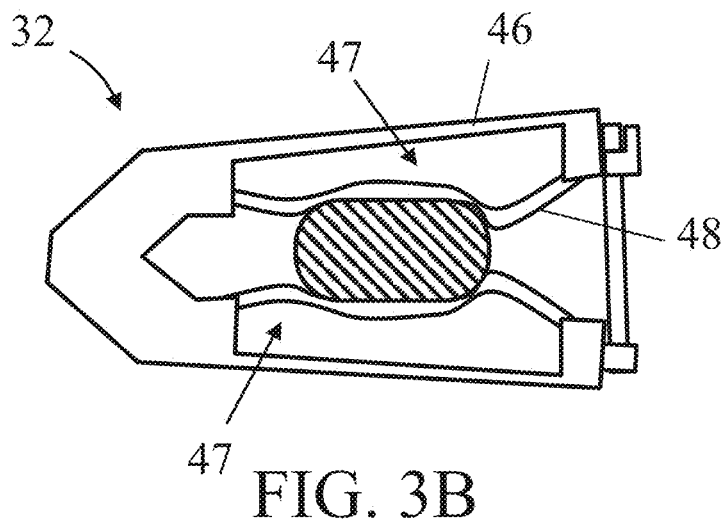
Figure 3C:
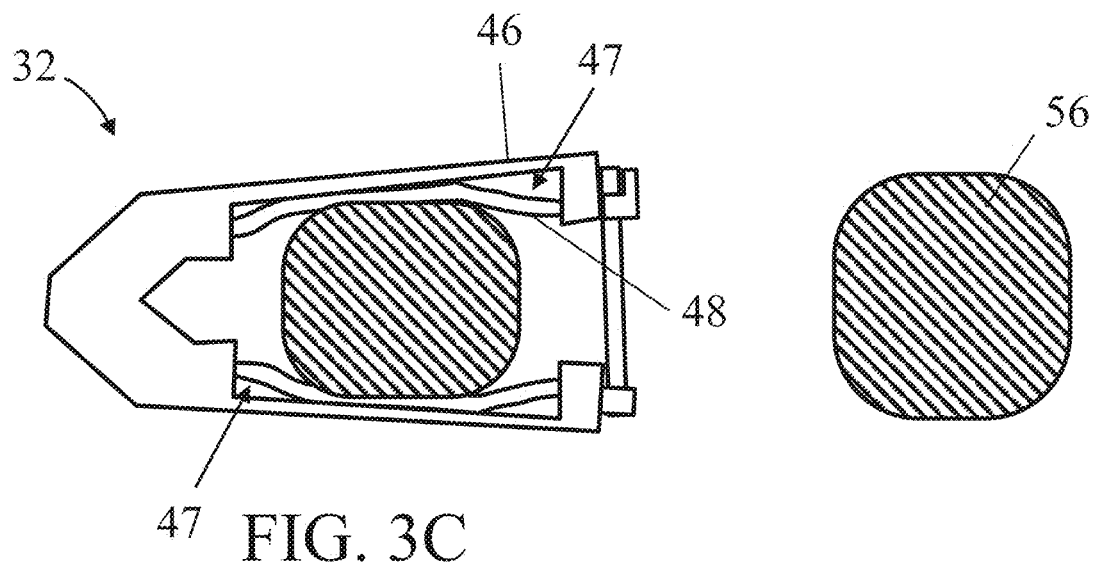

Reference is now made to FIGS. 3A-3C, which schematically illustrate a side view of the hemostatic clip 32 in accordance of an embodiment of the invention. Similar to hemostatic clip 10, hemostatic clip 32 is thickness adjustable and is compatible to various tissue thicknesses. The gap 47 enclosed between outer rigid clip arm member 46 and inner resilient elastic clip arm member 48 is sized for accommodating various bodily tissue or organ thicknesses and may be reshaped according to the conformity of the inner resilient elastic clip arm member 48 to the bodily tissue or organ.

Referring to FIG. 3A, which illustrates thin bodily organ or tissue 52 conformity of hemostatic clip 32, gap 47 enclosed by outer rigid clip arm member 46 and inner resilient elastic clip arm member 48 may be slightly narrowed following tissue ligation.

Referring to FIG. 3B, which illustrates moderate thickness tissue 54 conformity of hemostatic clip 32, gap 47 enclosed by outer rigid clip arm member 46 and inner resilient elastic clip arm member 48 may be moderately narrowed, and/or inner resilient elastic clip arm member 48 may outwardly bend toward the outer rigid clip arm member 46.

Referring to FIG. 3C, which illustrates thick tissue conformity 56 of hemostatic clip 32, gap 47 enclosed by outer rigid clip arm member 46 and inner resilient elastic clip arm member 48 may be substantially narrowed or completely diminished. Optionally, inner resilient elastic clip arm member 48 may outwardly bend toward the outer rigid clip arm member 46 until at least part of the roof contact surface of inner resilient elastic clip arm member 48 contacts at least part of the inner surface of outer rigid clip arm member 46.

Figure 4:
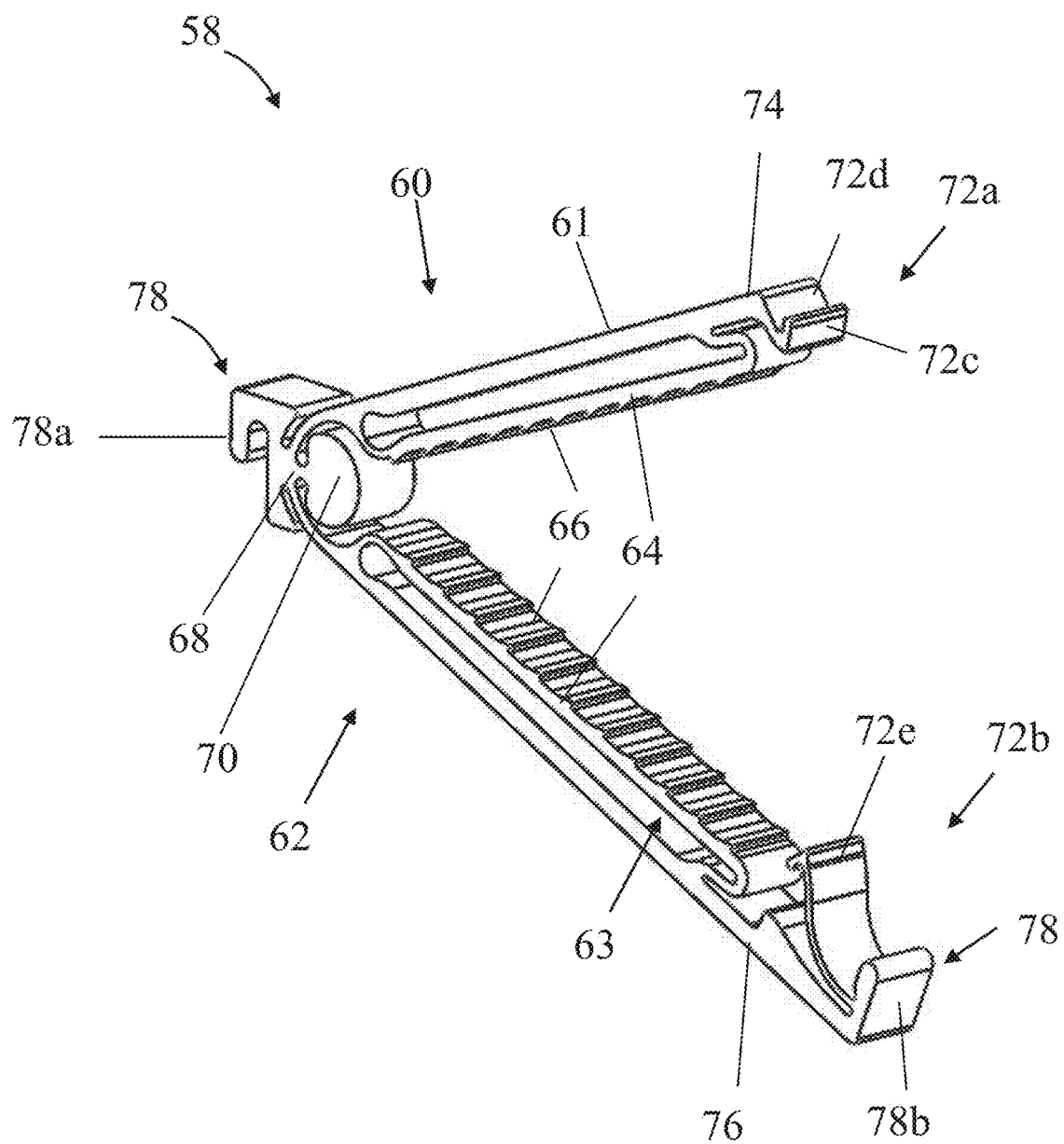
FIG. 4 is a schematic isometric view of an exemplary hemostatic clip, in accordance with some embodiments of the invention.

Reference is now made to FIG. 4, which is an isometric view of hemostatic clip 58. Hemostatic clip 58 is an exemplary hemostatic clip 32 and includes a first clip arm 60 (corresponds to clip arm 34 of hemostatic clip 32) and a second clip arm 62 (corresponds to clip arm 36 of hemostatic clip 32), each includes inner resilient clip arm member 64 (corresponds to inner resilient clip arm 48 of hemostatic clip 32). The inner resilient clip arm member 64 includes a tissue contacting surface 36 disposed with teethes. Clip arms 60 and clip arm 62 are connected via an integrally formed hinge 68. Hemostatic clip 58 further includes a barrier 70 for blocking tissue from entering into hinge 68.

Hemostatic clip 58 includes a locking mechanism 72 which includes a hook first end 72a connected to first clip arm distal end 74 and a hook second end 72b connected to second clip arm distal end 76. The hook is having a hook flange 72c positioned on first clip arm distal end 74 which is adapted for slidably engaging a cam surface 72e provided on the second clip arm distal end 76. Locking mechanism 72 is activated in response to the first clip arm 60 and the second clip arm 62 shifting from the non-stressed fully opened configuration to the stressed locked configuration. First and second clip arms 60 and 62 shift into the stressed locked configuration following hook flange 72e reaching and fitting into a niche 72d positioned beyond flange 72c.

In some embodiments, first and second clip arms 60 and 62, and locking mechanism 72, are integrally structured and manufactured from a single piece of material. In some embodiments, first and second clip arms 60 and 62, and locking mechanism 72, are manufactured from different materials.

In some embodiments, the material may be any suitable material, including, but not limited to polymers, metals, metal alloys (e.g. nickel-titanium, stainless steel, cobalt chrome, Titanium), or a combination thereof.

Hemostatic clip 58 may further include an interconnecting mechanism 78 configured for sequentially chaining lengthwise, one after another, a plurality of hemostatic clips 58. Interconnecting mechanism 78 includes a head coupler 78b that may be positioned at the distal end of clip arm 60 or clip arm 62. Interconnecting mechanism 78 further includes a tail coupler 78a that may be positioned at the proximal end of clip 58. When a plurality of clips 58 are aligned sequentially and lengthwise, head coupler 78a of one clip 58 may connect another clip 58 via tail coupler 78b of the other clip 58 and thereby chain one after another, a plurality of hemostatic clips 58.

Figure 5:
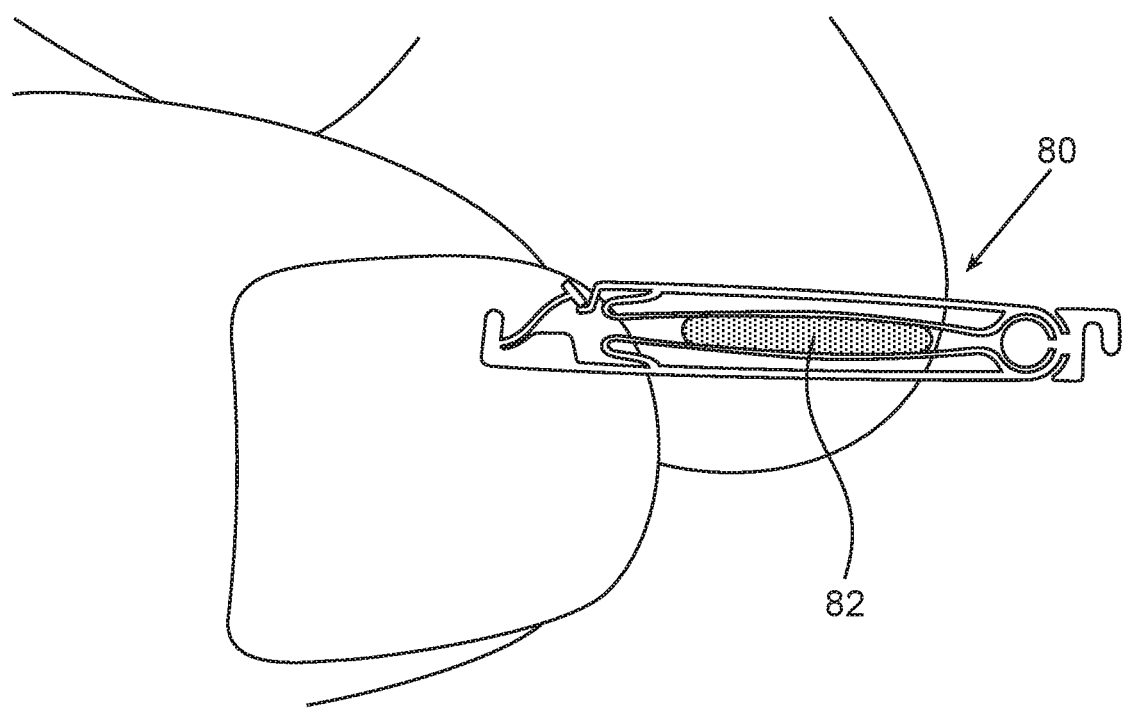
FIG. 5 is a photographic image of an exemplary hemostatic clip held in, and shown relative to, human fingers, in accordance with some embodiments of the invention.

Reference is made to FIG. 5, which is a photographic image of an exemplary hemostatic clip 80 held in human fingers. The image shows the relative size of the hemostatic clip relative to that of human fingers.

An aspect of some embodiments of the present invention is provision of a clip applier for deploying hemostatic clips onto a bodily organ or tissue in a subject. In exemplary embodiments, the clip applier includes: at least one thickness-adjustable hemostatic clip, including a distal-most thickness-adjustable hemostatic clip, with: a first clip arm having a first clip arm distal end; a second clip arm having a second clip arm distal end, movable relative to the first clip arm from a non-stressed fully opened clip configuration of the distal-most hemostatic clip; and a locking mechanism configured for locking the first clip arm distal end to the second clip arm distal end, so as to prevent self-opening of the hemostatic clip.

In such exemplary embodiments, at least one of the first and second clip arms includes an outer rigid clip arm member connected to an inner resilient elastic clip arm member having a tissue contacting surface, such that when deployed, the clip arm members are configured for applying clamping forces to a bodily organ or tissue via each inner resilient elastic clip arm member while allowing each inner resilient elastic clip arm member to compress or shift laterally towards a respective rigid outer clip arm member. In response to the deployment, the first and second clip arms conform to a compressed shape of the bodily organ or tissue.

Additionally, in such exemplary embodiments, the clip applier also includes a trigger mechanism having an inner sleeve and configured for sliding and advancing the inner sleeve from a retracted position that uncovers the distal-most hemostatic clip, to a protruding position that covers the distal-most hemostatic clip. According to such embodiments, the inner sleeve, when advanced to the protruding position over the first and second clip arms of the distal-most hemostatic clip, effects moving of the first and second clip arms to approach each other so as to self-lock the first and second clip arms by the locking mechanism of the distal-most hemostatic clip.

Another, related, aspect of some embodiments of the present invention is provision of a clip applier for ligating a bodily organ or tissue in a subject. In exemplary embodiments, the clip applier includes: at least one hemostatic clip, including a distal-most hemostatic clip, with: a first clip arm having a first clip arm distal end; a second clip arm having a second clip arm distal end, the second clip arm opposes and is pivotally linked to the first clip arm at a shared proximal end, and the second clip arm is movable relative to the first clip arm from a non-stressed fully opened clip configuration of the distal-most hemostatic clip; and a locking mechanism configured to lock together the first and second clip arm distal ends to a closed clip height being smaller than an opened clip height of a non-stressed fully opened clip configuration.

In such exemplary embodiments, the clip applier further includes a clip pressing mechanism, having a sliding press, and configured for selectively moving the sliding press across the distal-most hemostatic clip between a fully retracted position proximal to the distal-most hemostatic clip, and a fully protruded position across the distal-most hemostatic clip, so as to limit the opened clip height of the distal-most hemostatic clip to a maximal opened clip height being equal to or less than the closed clip height.

According to such exemplary embodiments, when the clip applier is deployed, shifting the sliding press from a retracted position to the fully protruded position effects gradual closing of the hemostatic clip by decreasing distance between the first and second clip arm distal ends, at least until reaching the closed-clip height, so as to activate the locking mechanism to lock together the first and second clip arm distal ends at the closed clip height, for facilitating ligation of the bodily organ or tissue.

Reference is now being made to FIGS. 6A-6D, which illustrate a clip applier 84 for deploying hemostatic clips onto a bodily organ or tissue. The description below refers to clip 58 for exemplary reasons only, however, the description equally applies for deploying any of the clips described herein. Clip applier 84 may house approximately 20 hemostatic clips, or any number of clips below 20 clips.

Clip applier 84 may include a housing, optionally in a form of a cannula, or an outer sleeve 86b, that is configured for housing multiple clips or/and for facilitating a passage or entry for applying clips to internal organs or tissues, optionally from outside treated subject's body. In some embodiments, the outer sleeve 86b may be in the form of a needle with a sharp edge for enabling piercing through a body cavity wall. In accordance with those embodiments, outer sleeve includes a first distal sharp end and a second distal blunt end.

As shown, a sliding press in a form of an inner sleeve 86a is provided, being capable of sliding and retracting from a fully protruded configuration in which clip 58 is fully covered and is in a stressed locked configuration (FIG. 6A) to a retracted position that uncovers hemostatic clip 58 (FIG. 6B), optionally motion is relative to a static position for outer sleeve 86b. In some embodiments, inner sleeve 86a may have a diameter which is sufficiently narrow to facilitate a closed and unlocked configuration of clip 58. For example, the diameter of inner sleeve 86a may be in a range between 0.2 mm and 5 mm.

Figure 6A:
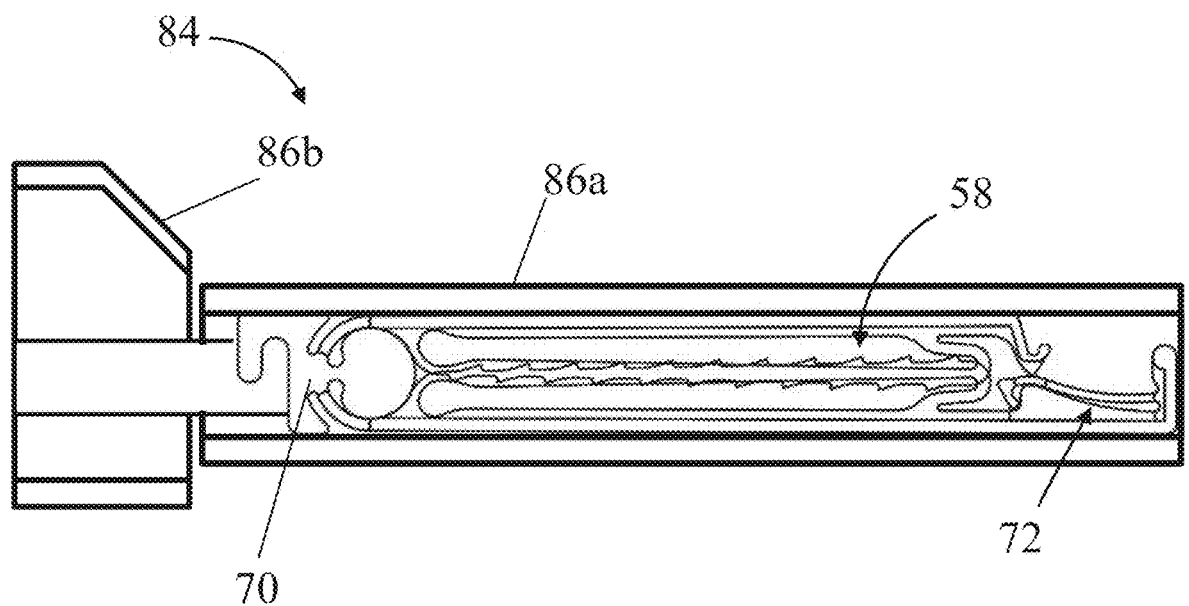
FIGS. 6A-6D are schematic side cut views of a portion of a clip applier which includes a hemostatic clip confined within a sleeve, wherein the clip is stressed locked and the sleeve is in a fully protruded configuration (FIG. 6A), the clip is in a fully opened non-stressed configuration and the sleeve is in a retracted configuration (FIG. 6B), the clip is in a closed and about to be locked, and the sleeve is in a partially protruded configuration (FIG. 6C), and the clip is in a stressed locked configuration and the sleeve is in a partially retracted configuration (FIG. 6D), in accordance with some embodiments of the invention.
Figure 6B:
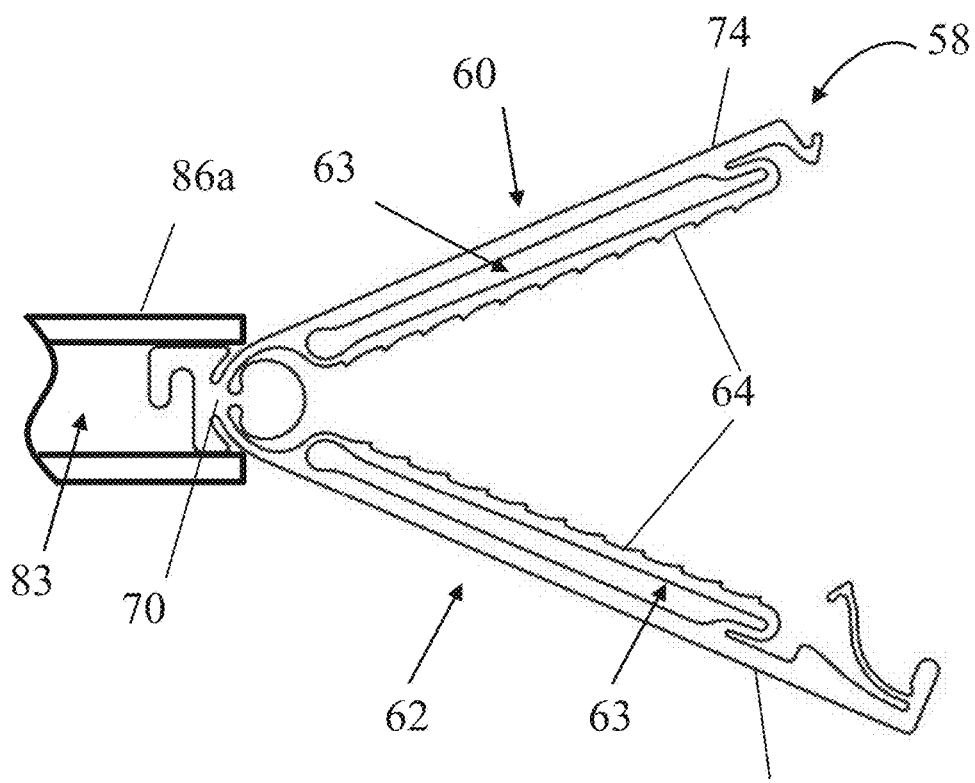
Figure 6C:
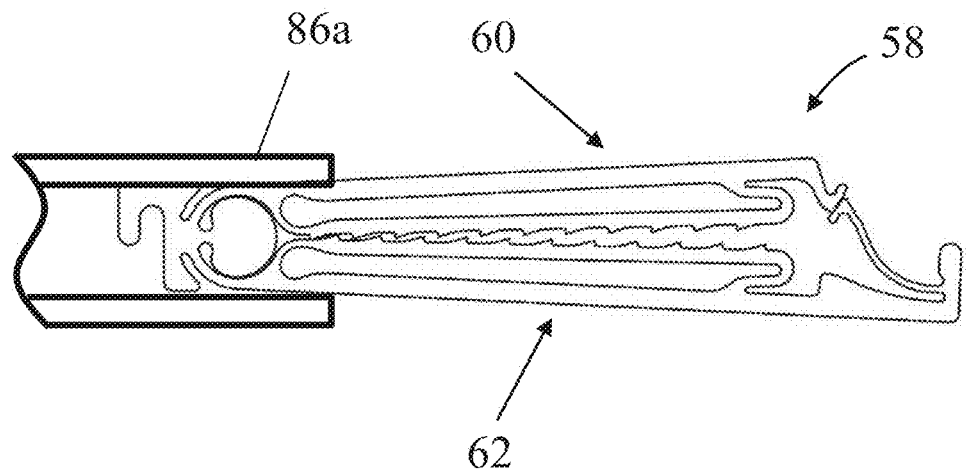
Figure 6D:
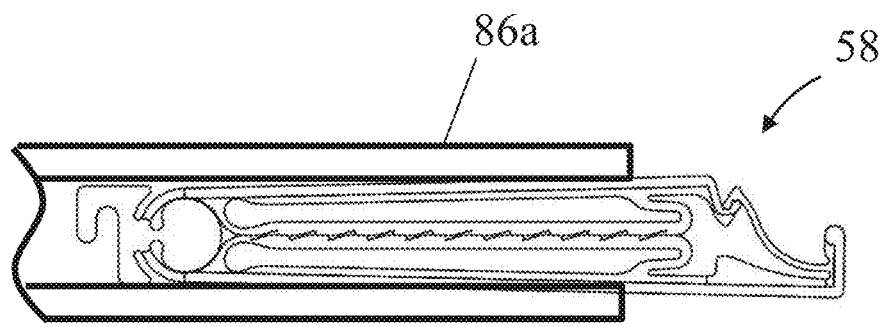

Optionally, alternatively or additionally, inner sleeve 86a is capable of sliding and advancing from a retracted position that in which hemostatic clip 58 uncovered or partially uncovered (FIGS. 6B and 6C), to a protruding position that covers hemostatic clip 58 and thereby effects locking of clip 58 (FIG. 6D). Locking clip 58 is mediated following gradual advancing and sliding to a protruding position of sleeve 86a (FIGS. 6C and 6D) which gradually covers first and second clip arms 60 and 62 of hemostatic clip 58. Sleeve 86a effects moving of the first and second clip arms 60 and 62 to approach each other so as to self-lock hemostatic clip 58 by locking mechanism 72.

In some embodiments, inner sleeve 86a includes opposing tracks. In some embodiments, opposing tracks are sized and shaped for accommodating runner surfaces of the first and second clip arms 60 and 62 in contact therewith. In some embodiments, opposing tracks are parallel to each other.

In some embodiments, inner sleeve 86a includes a slot 83 provided along each side thereof, opened to distal opening thereof. Slots 83 are required in order to pass inner sleeve 86a along a length of a grasped or ligated bodily organ or tissue without causing damage or even be in contact therewith during travel (distal-protruding or proximal-retracting, relative to hemostatic clip 58). In some embodiments, length of each slot 83 is equal to or greater than the length of most or all of hemostatic clip 58, optionally at least its functionally effective length between hinge 70 and locking mechanism 72. In some embodiments, height of each slot 83 is equal to or greater than a maximal compressed thickness of a grasped or ligated bodily organ or tissue when hemostatic clip 58 is in a locked configuration. Alternatively, or additionally, height of each slot 83 is equal to or grater than a total height of a gap 63 between inner 64 and outer 62 clip arm members, optionally, about 5 mm or more, or optionally, about 8 mm or more.

In some embodiments, a trigger mechanism 86 (comprising at least inner sleeve 86a) is shaped and sized for forcing first and second inner resilient elastic clip arm members 64 to align in a predetermined formation in which distance between the first and second clip arm distal ends 74 and 76 is equal to or less than a predetermined opening. In some embodiments, the term "predetermined opening" is interchangeable with the term "predetermined distance".

Figure 7:
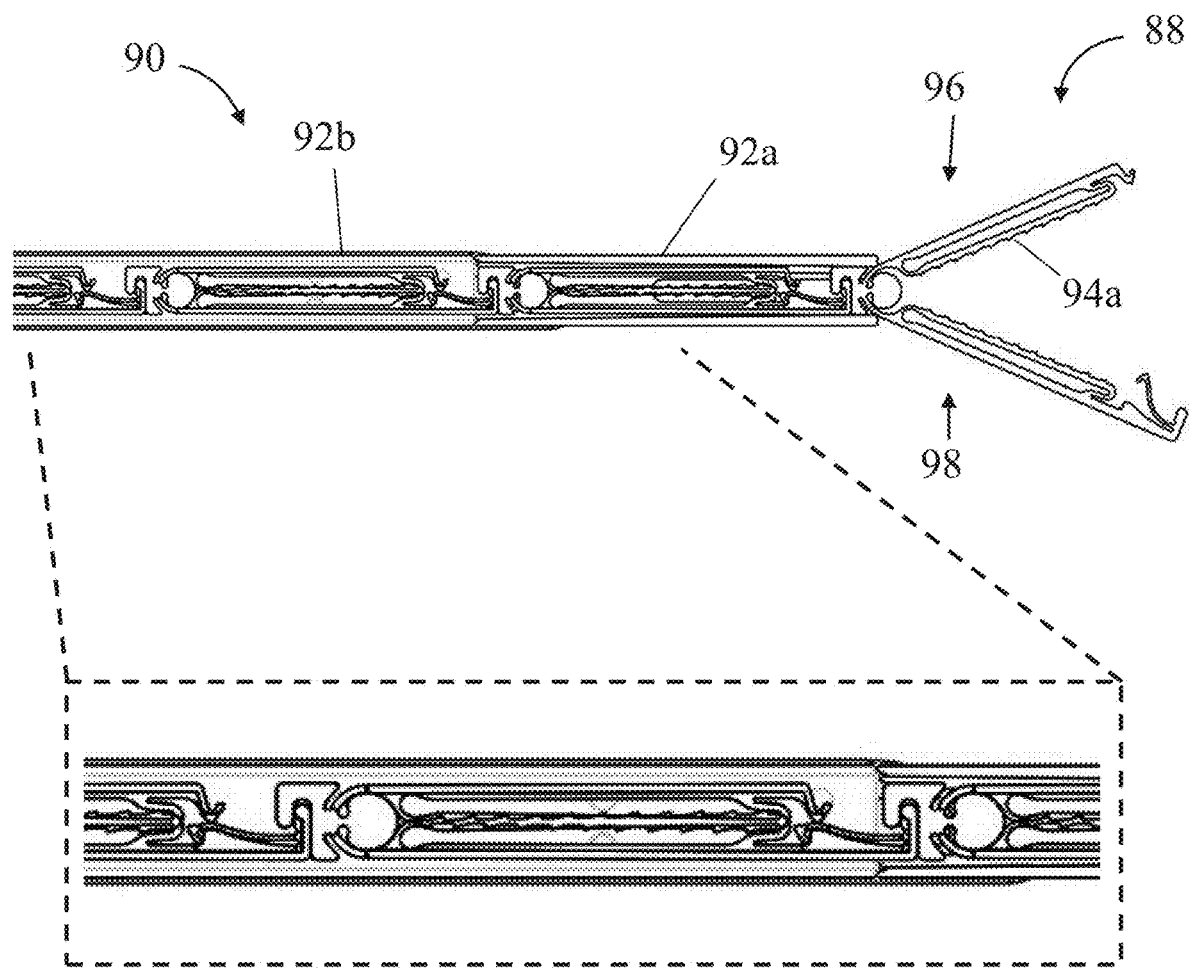
FIG. 7 is a schematic side cut view of another exemplary clip applier, in accordance with some embodiments of the invention.

Reference is now being made to FIG. 7, which illustrates another exemplary clip applier 90 for deploying hemostatic clips onto a bodily organ or tissue and ligating the bodily organ or tissue. The description below refers to hemostatic clip 88 (described in details below) for exemplary reasons only, however, the description of FIG. 7 equally applies for deploying any of the clips described herein.

Similar to clip applier 84, clip applier 90 may house multiple hemostatic clips 88. In some embodiments, hemostatic clips are positioned in clip applier 90 in a closed and unlocked configuration. Clip applier 90 includes a clip pressing mechanism, including sliding press 92, configured for laterally sliding and advancing. In some embodiments, sliding press 92 includes a tubular member 92a which is in a form of an inner sleeve (optionally similarly to inner sleeve 86a) and is capable of axially sliding in a lumen of an outer sleeve 92b. In some embodiments, tubular member 92a and outer sleeve 92b are movable one towards the other. Outer sleeve 92b may be in a form of a needle or may include a sharp edge in its distal end. In some embodiments, tubular member 92a includes an inner lumen dimensioned for limiting opening of hemostatic clip 88 to the opened configuration.

Clip applier 90 may include a biasing mechanism 94 provided within hemostatic clip 88. Biasing mechanism 94 is provided between the first and second clip arms 96 and 98. Biasing mechanism 94 is configured for compressing the ligated bodily organ or tissue when hemostatic clip 88 is being locked. Biasing mechanism 94 may include an inner clip arm member 94a. In some embodiments, inner clip arm member 94a corresponds and/or is essentially similar to inner resilient elastic clip arm members 20 and/or 48 and/or 64 of hemostatic clips 10, 32 and 58, respectively. The remaining elements of hemostatic clip 88 are essentially similar to the elements of hemostatic clips 10, 32 and 58.

Figure 8:
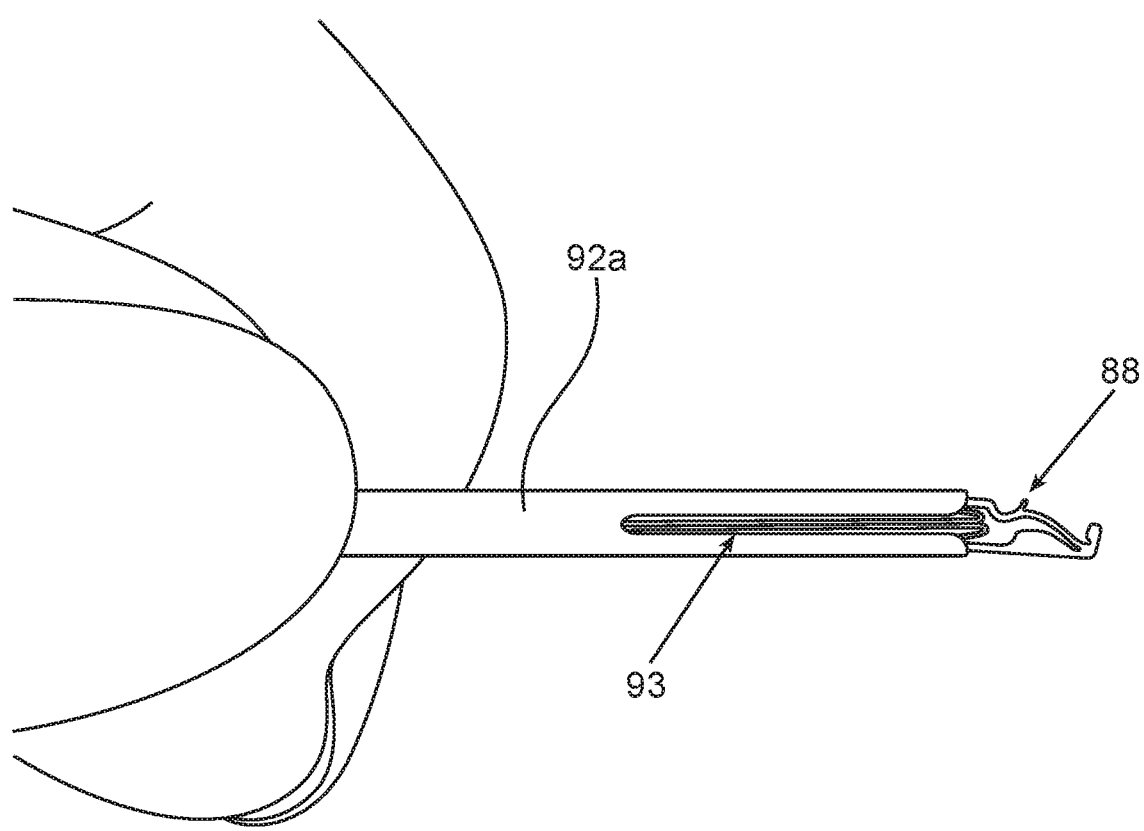
FIG. 8 is a photographic image of an exemplary hemostatic clip confined within a sleeve of a hemostatic clip, when held in between human fingers, in accordance with some embodiments of the invention.

Reference is made to FIG. 8, which is a photographic image of an exemplary clip 88 confined within tubular member 92a held in between human fingers. The image shows the relative sizes of the clip and clip applier, both relative to that of human fingers. In some embodiments, tubular member 92a includes a slot 93 provided along each side of tubular member 92a, opened to distal opening thereof. In some embodiments, length of each slot 93 is equal to or greater than the length of most or all hemostatic clip 88, optionally at least its functionally effective length between hinge and locking mechanism of clip 88. In some embodiments, height of each slot 93 is equal to or greater than a maximal compressed length of a grasped or ligated bodily organ or tissue when hemostatic clip 88 is in a locked configuration, or/and optionally about 5 mm or more, or optionally about 8 mm or more.

Figure 9:
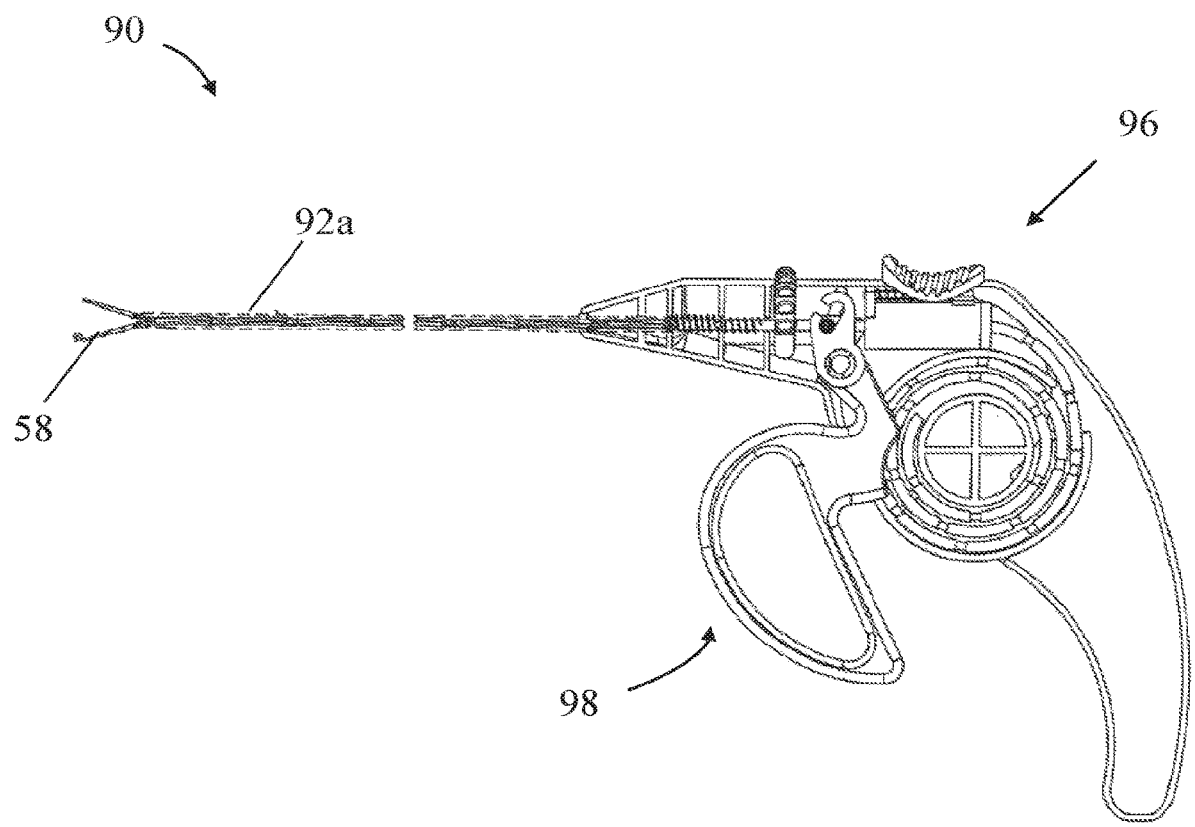
FIG. 9 is a side cut view illustration of a clip applier which includes a handle for operating the hemostatic clips of the invention.

Reference is made to FIG. 9, which illustrates a clip applier 90 which further includes a handle 96 and a trigger 98 configured for operating the hemostatic clips of the invention. The description below refers to hemostatic clip 58 and clip applier 90 for exemplary reasons only, however, the description of FIG. 9 equally applies any of the clips and clip appliers described herein. Handle 96 may include a mechanism for maneuvering tubular member 92a with respect to the clips housed in the tubular member 92a. The tubular member 92a maneuvering mechanism may include a trigger 98, extending from handle 96, for moving tubular member 92a, to deploy any of the clips described above. The most distally positioned clip 58 housed in tubular member 92a may be exposed from the distal end of tubular member 92a and positioned for deployment via any suitable clip advancement method. The handle and its operating system have been disclosed, by the same applicant of the present disclosure, in International Patent Application Publication No. WO 2015/040621.

Another aspect of some embodiments of the present invention is a method of ligating a bodily organ or tissue in a subject. The herein disclosed bodily organ or tissue ligating method may be practiced and implemented using any of the herein illustratively described exemplary embodiments of the hemostatic clip applier (and, components and features thereof), for example, clip applier 84 shown in at least FIGS. 6A-6D, and clip applier 90 shown in at least FIGS. 7 and 9. Moreover, the herein disclosed bodily organ or tissue ligating method may be practiced and implemented using any of the herein illustratively described exemplary embodiments of the hemostatic clip (and, components and features thereof), for example, clip 10, clip 32, clip 58, clip 80, clip 88, clip 120, or clip 120', shown in the figures.

FIG. 10 is a flow diagram of an exemplary embodiment (indicated as, and referred to by, reference number 100), including the indicated exemplary steps (procedures/processes) thereof, of a method of ligating a bodily organ or tissue in a subject. In FIG. 10, the exemplary embodiment 100 of the bodily organ or tissue ligating method includes exemplary steps (procedures/processes) represented by separate blocks (frames) which are assigned reference numbers, for example, 104, 108, 112, etc. As shown in FIG. 10, in a non-limiting manner, and in some embodiments, such as exemplary embodiment 100, the method of ligating a bodily organ or tissue in a subject includes the following exemplary steps (procedures/processes).

In 104, there is providing a distal-most hemostatic clip configured for surrounding the bodily organ or tissue, wherein the distal-most hemostatic clip includes a first clip arm having a first clip arm distal end and a second clip arm having a second clip arm distal end, the second clip arm opposes and is pivotally linked to the first clip arm at a shared proximal end, and the second clip arm is movable relative to the first clip arm from a non-stressed fully opened clip configuration of the distal-most hemostatic clip.

In 108, there is providing a biasing mechanism between the first and second clip arms and allowing the biasing mechanism to occupy a space between the first and second clip arms and the bodily organ or tissue.

In 112, there is gradually closing the hemostatic clip over the bodily organ or tissue by forcibly decreasing distance between the first and second clip arm distal ends.

In 116, there is locking together the first and second clip arm distal ends to a closed clip height, via activating a locking mechanism.

In exemplary embodiments of the bodily organ or tissue ligating method, the steps (procedures) of gradually closing the hemostatic clip or/and of locking together the clip arm distal ends effect the biasing mechanism into compressing and clamping the bodily organ or tissue, while being deformed at least partially into an outer periphery of the compressed and clamped bodily organ or tissue.

In exemplary embodiments of the bodily organ or tissue ligating method, a hemostatic clip and a clip applier, as described herein are provided. A hemostatic clip being most distally positioned within a clip applier is provided with the two arms of the clip being opened (unlocked). In some embodiments, the clip may be in a fully closed (locked configuration. The clip is then provided to surround a bodily organ or tissue. The hemostatic clip is gradually closed over the bodily organ or tissue by forcibly decreasing a distance between a first and a second clip arms distal ends, and by activating a locking mechanism to thereby lock together the first and second clip arm distal ends to a closed clip configuration.

In exemplary embodiments, the gradually closing or/and locking may be effected by a biasing mechanism of the hemostatic clip which compresses and clamps an outer periphery of the bodily organ or tissue to thereby deform and ligate the bodily organ or tissue. In exemplary embodiments, a biasing mechanism includes at least one inner resilient arm member connected to a clip arm member. In exemplary embodiments, gradually closing and/or locking may further be effected by shifting sliding press provided in the clip applier from a fully retracted position, proximal to the distal-most hemostatic clip, to a fully protruded position, distal to the distal-most hemostatic clip. In exemplary embodiments, shifting from a fully retracted position, proximal to the distal-most hemostatic clip, causes the height between the distal ends of the two clip arms to be reduced and limited to the closed and locked position of the clip. In exemplary embodiments, shifting the sliding press to the fully protruded position over the hemostatic clip initiates activating of the locking mechanism of the hemostatic clip. In exemplary embodiments, the distal-most hemostatic clip is ejected from the clip applier. In exemplary embodiments, the releasing and ejecting is effected by retracting the sliding press to the fully retracted position.

Reference is made to FIGS. 11A-11G, which schematically illustrate steps (procedure/processes) of practicing and implementing the herein disclosed exemplary method of ligating a bodily organ or tissue in a subject, using, for example, clip applier 90. The description below refers to hemostatic clip 58 for exemplary purpose only. In a non-limiting manner, the below description equally applies to deploying any of the clips described herein.

Figure 11A:
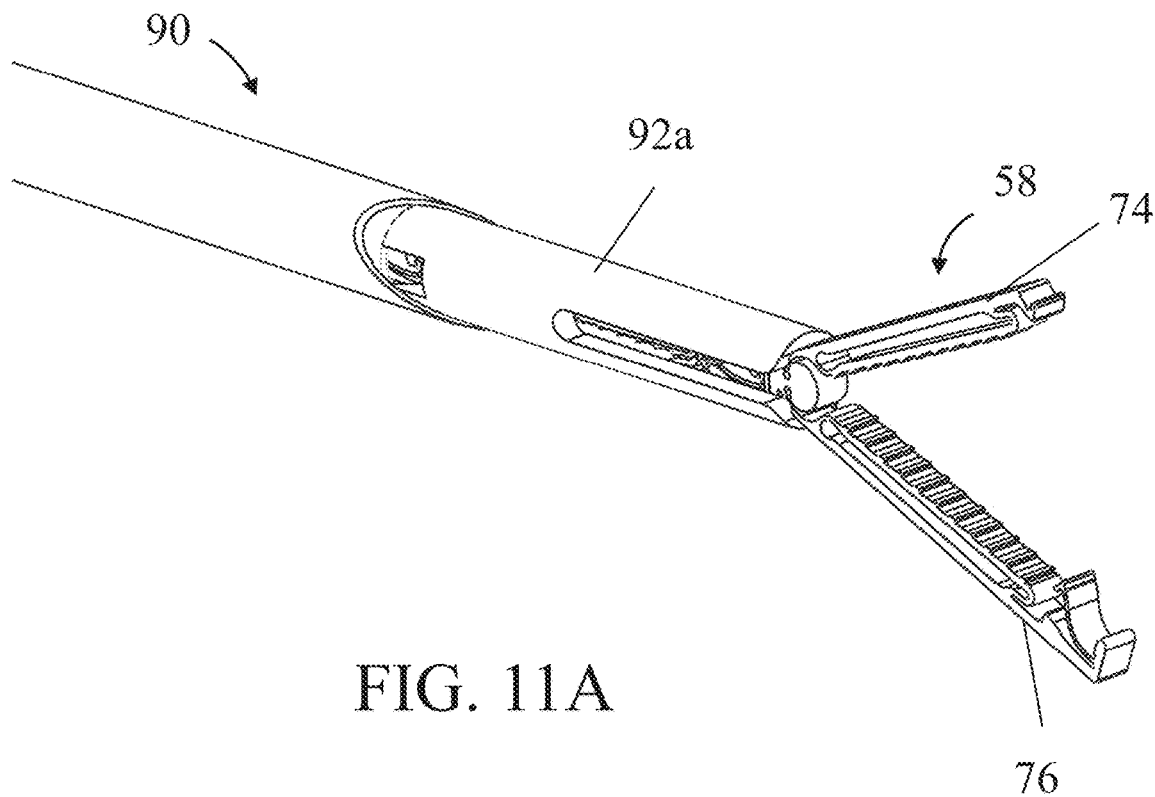
FIGS. 11A-11G schematically illustrate steps (procedures/processes) of implementing the herein disclosed exemplary method of ligating a bodily organ or tissue in a subject, highlighting an exemplary clip applier during various stages of tissue ligation, in accordance with some embodiments of the invention.

Referring to FIG. 11A, clip 58 is shown in a fully opened configuration. Tubular member 92a is in a retracted configuration. Clip 58 is opened to its maximal opened clip height.

Figure 11B:
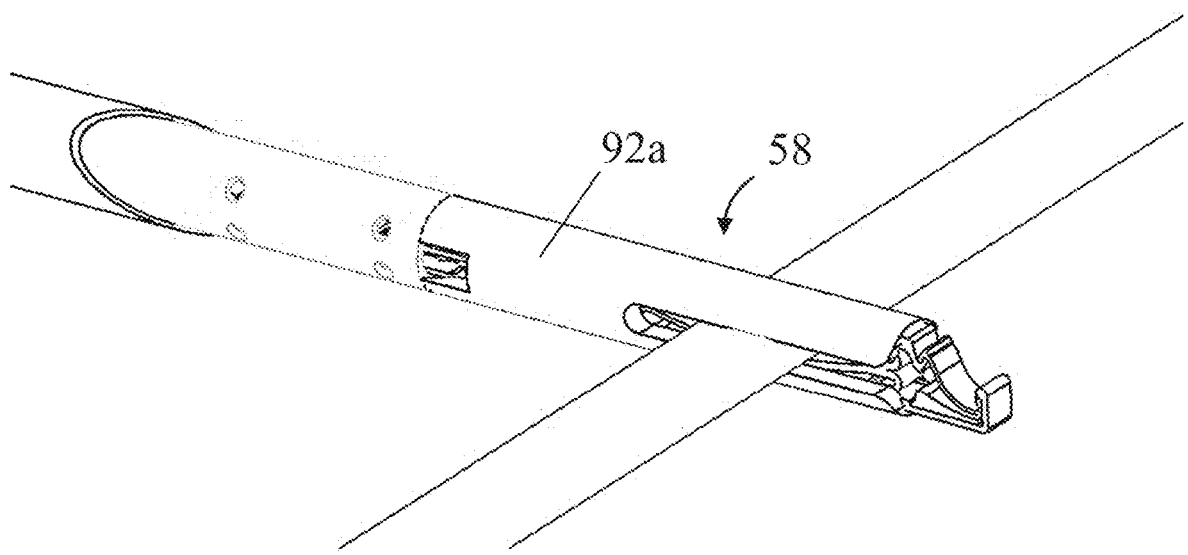
Figure 11C:
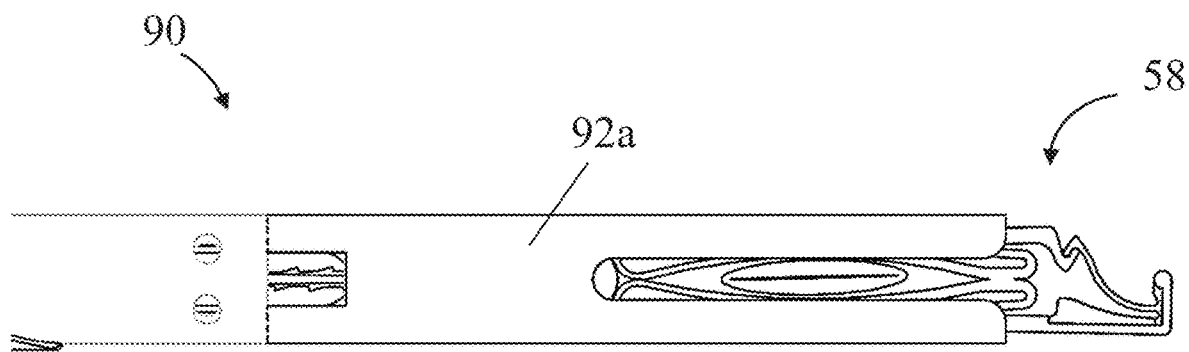
Figure 11D:
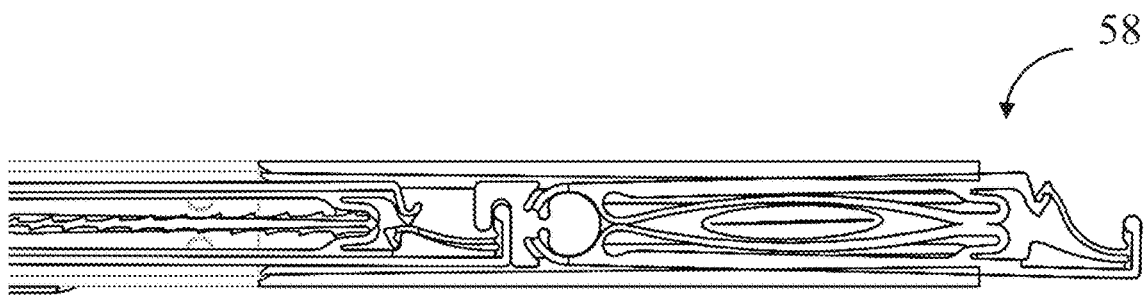

Referring to FIGS. 11B-11D, tubular member 92a may be moved across distal most hemostatic clip 58 to gradually shift to a fully protruded position. Shifting the tubular member 92a from a retracted position to the fully protruded position effects gradual closing of the hemostatic clip 58 over a bodily organ or tissue by decreasing distance between the first and second clip arm distal ends 74 and 76, at least until reaching a closed-clip height, so as to activate locking mechanism 72 to lock together the first and second clip arm distal ends 74 and 76.

Figure 11E:
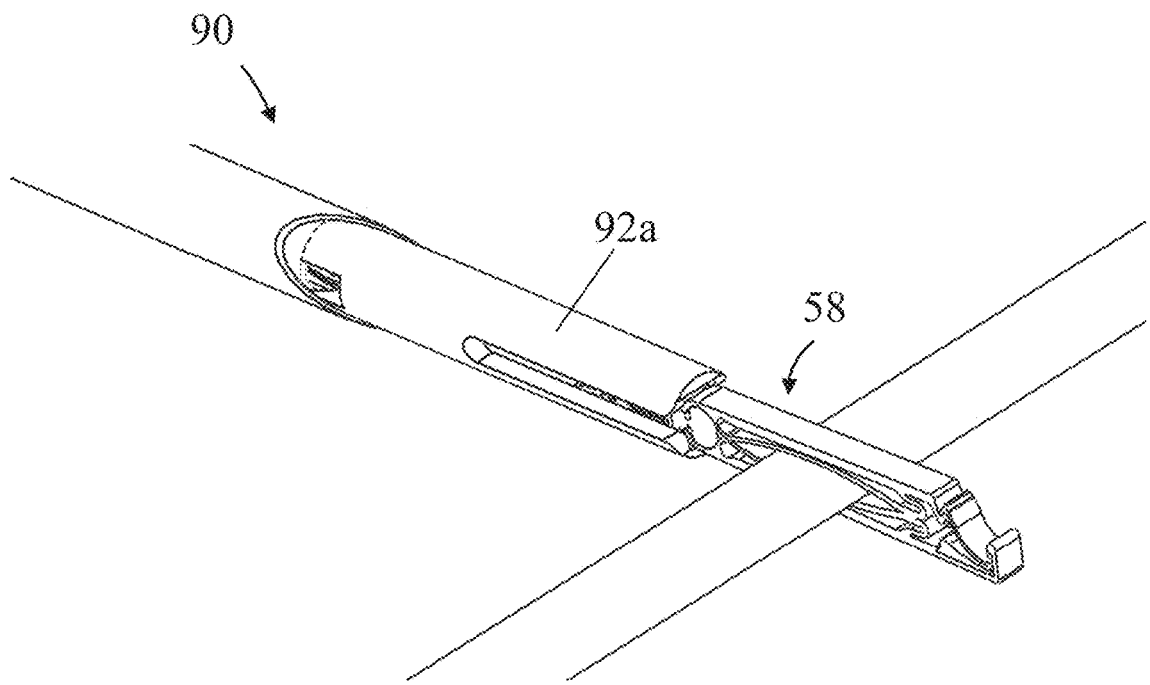
Figure 11F:
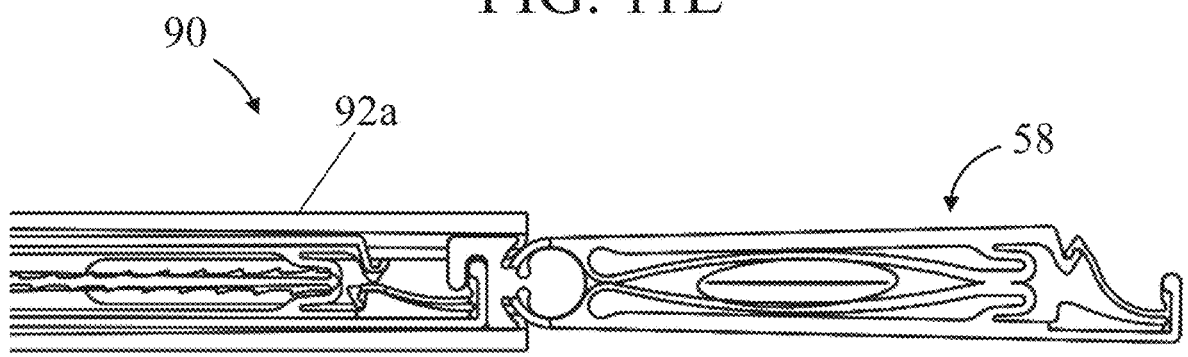
Figure 11G:

Referring to FIGS. 11E-11G, ejection of the distal-most hemostatic clip 58 is shown. Retraction of tubular member 92a to the fully retracted position when the first and second clip arm distal ends 74 and 76 are locked together effects release and ejection of the distal-most hemostatic clip 58.

In some embodiments, the hemostatic clip is configured for ligating an object (organ or a tissue) by applying variable pressure gradient along its length (i.e., along longitudinal axis thereof) using an inner clip arm member with variable axial resistance to deform under forces applied thereto, in ways which can improve fastening onto the object while allowing mutual conformity in shape. In some such embodiments, the clip is configured such that opposing inner clip arm members thereof each having a different axial resistance gradient, meaning that at different points along clip length each inner arm member is configured with a different, sometimes opposing (relative to average resistance) resistance to deformation.

In such or other embodiments, the hemostatic clip has at least one inner arm member having free end portions (i.e., unsupported extremities) so that contact with the ligated object can be facilitated throughout most or all effective length of the clip including adjacent to the clip ends, without interfering with function of other clip elements, such as the locking mechanism or/and the clip joint portion (shared proximal end), since that these free end portions are easily deformable or/and shiftable with minimal resistance to forces applied thereto relative to other portions of the inner clip arm member.

Figure 12A:
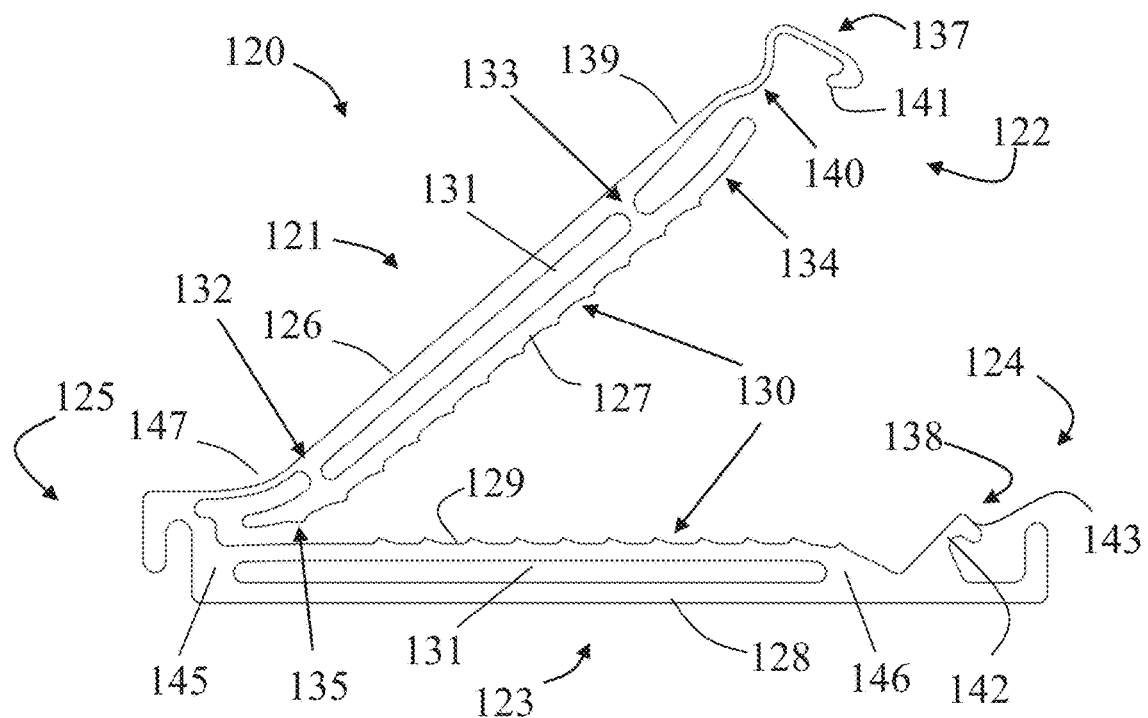
FIGS. 12A-12B are schematic side views of a first exemplary thickness-adjustable hemostatic clip having an inner clip arm member with free end portions, in accordance with some embodiments of the invention.
Figure 12B:
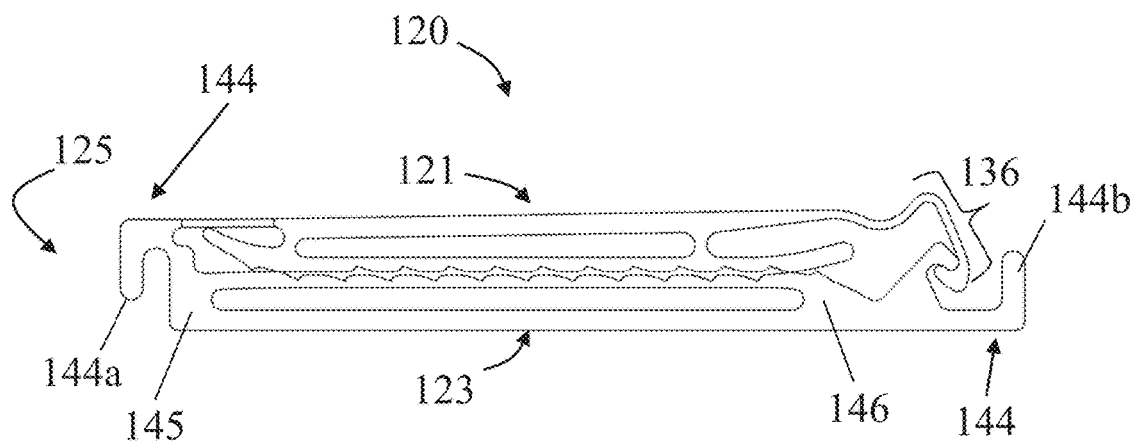

Reference is now made to FIGS. 12A-12B which are schematic side views of an exemplary thickness-adjustable hemostatic clip 120 having an inner clip arm member with free end portions. In some embodiments, hemostatic clip 120 is an exemplary variant of hemostatic clip 58, having similar structural and functional features, but differs in location of joining portions of one of its inner arm members to its corresponding outer arm member and formation of free end portions at both extremities thereof.

Hemostatic clip 120 includes a first clip arm 121 having a first clip arm distal end 122, and a second clip arm 123 having a second clip arm distal end 124. Second clip arm 123 opposes and is connected to first clip arm 121 at a shared proximal end 125, that is configured as an elastic normally-opened joint portion. First clip arm 121 includes a first outer clip arm member 126 connected to a first inner clip arm member 127, and second clip arm 123 includes a second outer clip arm member 128 connected to a second inner clip arm member 129. Each one of first and second inner clip arm members, 127 and 129, respectively, has a tissue contacting surface 130, and configured with a gap 131 formed with the respective outer clip arm member, such that the respective inner clip arm member can elastically deform or/and shift towards its respective outer clip arm member when first and second clip arms, 121 and 123, are closed against, and mutually apply compression and clamping forces to, a bodily organ or tissue. Each respective gap 131 is sized for accommodating inner clip arm member 127 or 129 that conforms to the bodily organ or tissue and outwardly bends toward respective outer clip arm member 126 or 128. In some embodiments, first inner clip arm member 127 is configured to apply a pressure of up to about 150 gr/mm$^2$ to the bodily organ or tissue that is grasped by hemostatic clip 120.

First inner clip arm member 127 is connected to first outer clip arm member 126, via a proximal first arm joining portion 132 and a distal first arm joining portion 133, and includes a distal end portion 134 that freely extends distally from distal first arm joining portion 133 and a proximal end portion 135 that freely extends proximally from proximal first arm joining portion 132.

Second inner clip arm member 129 is connected to second outer clip arm member 128, via a distal-most second arm joining portion 146 and a proximal-most second arm joining portion 145, such that second inner clip arm member 129 extends in full between distal-most second arm joining portion 146 and proximal-most second arm joining portion 145, such that proximal first arm joining portion 132 and distal first arm joining portion 133 are provided between distal-most second arm joining portion 146 and proximal-most second arm joining portion 145.

First inner clip arm member 127 is configured such that resistance to deformation or/and shift towards first outer clip arm member 126 is greater along an intermediate portion provided between distal end portion 134 and proximal end portion 135, than along any of distal end portion 134 and proximal end portion 135 of first inner clip arm member 127. Vice versa, second inner clip arm member 129 is configured such that resistance to deformation or/and shift towards second outer clip arm member 128 is smaller along its middle portion rather than along or towards any of its ends. This type of 'negative' or 'opposite' asymmetry of mechanical resistance along opposing tissue contacting surfaces 130 contributes to improved grasping alongside relieved stresses across grasped organ or tissue portion, relative to symmetric grasping.

A locking mechanism 136 provided with clip 120 is configured for locking together first clip arm distal end 122 to second clip arm distal end 124, when pressed against each other. Locking mechanism 136 includes a hook 137 with a hook flange 141, which is provided in a form of a distal extension of first outer clip arm member 126. Locking mechanism 136 also includes a niche 142 with a cam surface 143 in a form of a distal extension of second clip arm 123 (after joining of second inner and outer clip arm members 128 and 129), therefore it is more rigid and reluctant to deform relative to hook 137. Hook 137 extends from a relatively straight hook leg portion 139 originating from distal first arm joining portion 133 and extending distally across entire length of distal end portion 134, then it is curved towards first inner clip arm member 127 until a hook apex 140 provided distally and adjacent to distal end portion 134, then curved away into a form of a hook.

Distal end portion 134 of first inner clip arm member 127 is configured such that, when pressed against an organ or a tissue towards engaging with second clip arm 123, distal end portion 134 will flex towards hook leg portion 139, thereby supporting a length of hook leg portion 139 up to a point located adjacently and proximally to hook apex 140. Optionally, such additional support to hook 137 also facilitates a fortified hinge point, such that hook 137 is configured to flex towards engagement with flange 138 about this fortified hinge point. Hook flange 141 is shaped and configured to slidably engage along and beyond cam surface 143, then fasten to niche 142, when first and second clip arms 121 and 123 shift from an opened (unlocked) clip configuration (FIG. 12A) to a locked clip configuration (FIG. 12B).

Hemostatic clip 120 further includes an interconnecting mechanism 144, similar or identical in structure or/and function to interconnecting mechanism 78, configured for sequentially chaining lengthwise, one after another, a plurality of the hemostatic clip 120. Interconnecting mechanism 144 includes a tail coupler 144a, provided at hemostatic clip shared proximal end 125, which is connectable to a head coupler 144b, provided at second clip arm distal end 124.

Distal end portion 134 extends along a length greater than about 1 mm, optionally within a range of about 1 mm to about 3 mm, distally from distal first arm joining portion 133. Proximal end portion 135 extends along a length greater than about 0.5 mm, optionally within a range of about 0.5 mm to about 2 mm, proximally from proximal first arm joining portion 132.

Figure 13A:
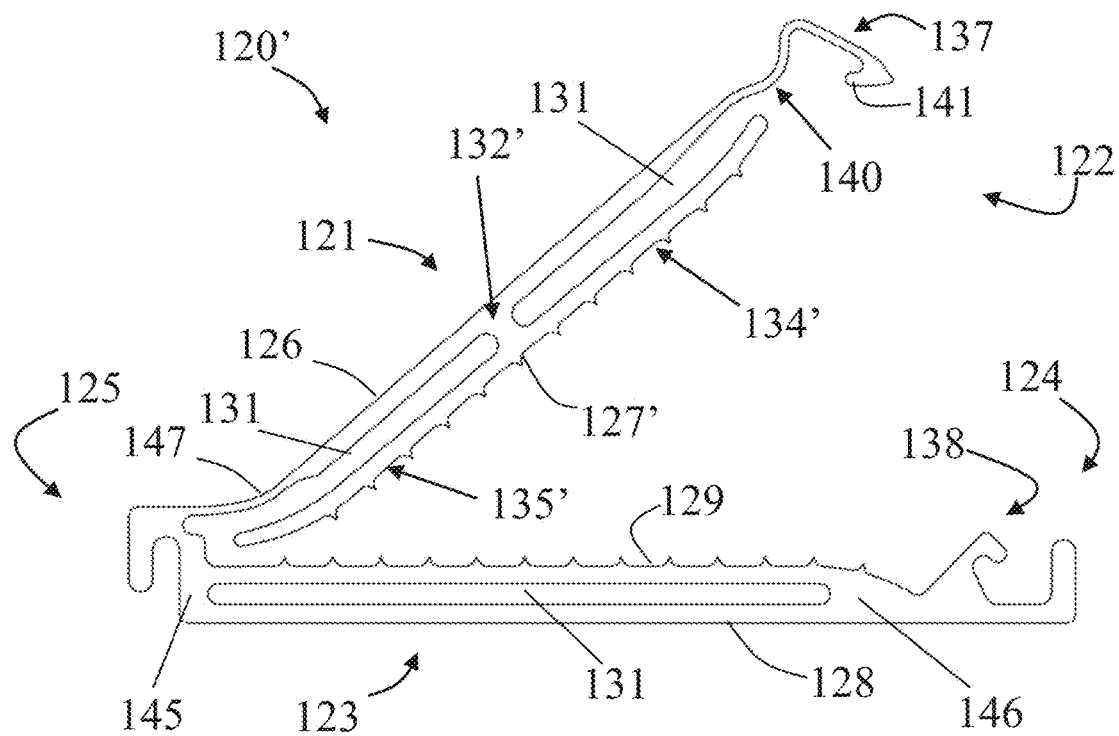
FIGS. 13A-13B are schematic side views of a second exemplary thickness-adjustable hemostatic clip having an inner clip arm member with free end portions, in accordance with some embodiments of the invention.
Figure 13B:
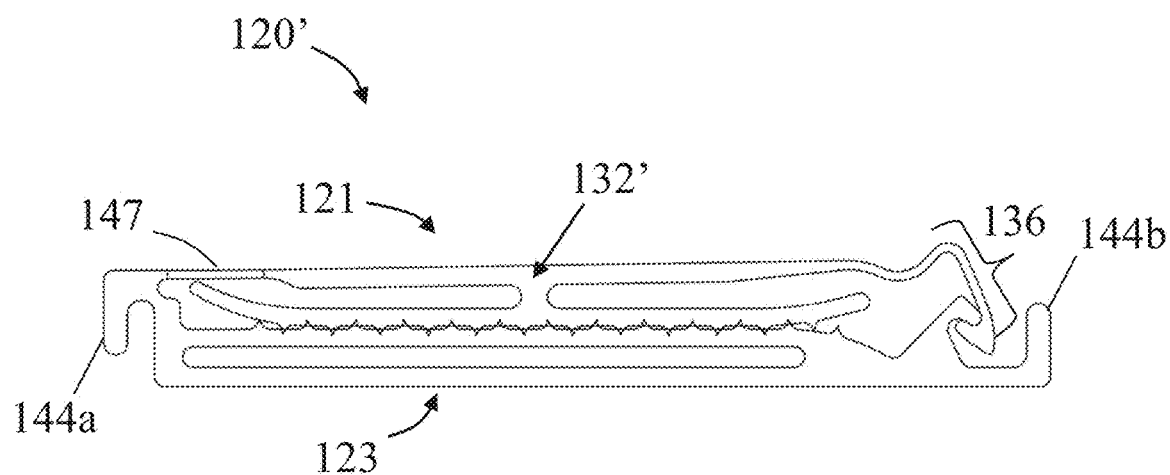

FIGS. 13A-13B are schematic side views of a second exemplary thickness-adjustable hemostatic clip 120' having an inner clip arm member with free end portions, which is a variation of hemostatic clip 120. FIG. 13A shown clip 120' in an opened configuration, and FIG. 13B shows the clip 120' in a closed, locked, configuration. Hemostatic clip 120' is similar or identical to hemostatic clip 120, however first inner clip arm member 127' thereof differs from first inner clip arm member 120 by having a single first arm joining portion 132', wherein both distal end portion 134' and proximal end portion 135' of first inner clip arm member 127' freely extend from the single first arm joining portion 132'. In this design both distal end portion 134' and proximal end portion 135' have longer unsupported lengths. At least one of distal end portion 134' and proximal end portion 135' of first inner clip arm member 127' extends along a length greater than about 3 mm, optionally greater than about 4 mm, from the single joining portion 132'. This design, relative to design shown in FIGS. 12A-12B, has even increased deviance in lengthwise gradient of resistance to deformation or shift, between first inner clip arm member 127' and second inner clip arm member 129.

In exemplary embodiments, each of entire hemostatic clip 120 (FIGS. 12A-12B) and entire hemostatic clip 120' (FIGS. 13A-13B), including at least first and second clip arms 121 and 123, and locking mechanism 136, is integrally structured and manufactured from a single piece of material or/and as product of a mutual manufacturing process (e.g., casting, printing or laser cutting). In exemplary embodiments, each of hemostatic clips 120 and 120' has a length within a range of 10 mm to 20 mm, optionally about 15 mm or less; and a height (when each clip 120 or 120' is in a closed and locked configuration) within a range of 1 mm to 3 mm, optionally about 2 mm or less. Each of hemostatic clips 120 and 120' has optionally a constant width (extending between sides of the respective hemostatic clip 120 or 120'), optionally within a range of 0.5 mm to 2 mm, optionally 1 mm to 1.5 mm, optionally about 1.1 mm. Thickness of some or most elements of hemostatic clips 120 and 120', which include at least one of first outer clip arm member 126, first inner clip arm member 127 and 127', second outer clip arm member 128 and second inner clip arm member 129, is optionally substantially constant or/and may vary within a range of 0.2 mm to 0.5 mm, optionally 0.3 mm to 0.4 mm. Optionally and additionally, some portions configured for greater flexibility (i.e., configured for less resistance to deformation or shift by external forces applied thereto), such as along length of hook 137 and flex portion 147 connecting first clip arm 121 and shared proximal end 125, have a smaller thickness, such as within a range of 0.1 mm to 0.2 mm, optionally about 0.15 mm or less. Optionally and additionally, some portions configured for greater stiffness (i.e., configured for more relative resistance to deformation or shift by external forces applied thereto), such as distal-most second arm joining portion 146 and proximal-most second arm joining portion 145, may have a greater thickness, such as above 0.4 mm.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'includes', and 'including', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to a single step, procedure, manner, means, or/and technique, or a sequence, set, or group of two or more steps, procedures, manners, means, or/and techniques, for accomplishing or achieving a given task or action. Any such herein disclosed method, in a non-limiting manner, may include one or more steps, procedures, manners, means, or/and techniques, that are known or readily developed from one or more steps, procedures, manners, means, or/and techniques, previously taught about by practitioners in the relevant field(s) and art(s) of the herein disclosed invention. In any such herein disclosed method, in a non-limiting manner, the stated or presented sequential order of one or more steps, procedures, manners, means, or/and techniques, is not limited to that specifically stated or presented sequential order, for accomplishing or achieving a given task or action, unless otherwise specifically defined or stated herein, or, unless the context clearly dictates otherwise. Accordingly, in any such herein disclosed method, in a non-limiting manner, there may exist one or more alternative sequential orders of the same steps, procedures, manners, means, or/and techniques, for accomplishing or achieving a same given task or action, while maintaining same or similar meaning and scope of the herein disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2' and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A thickness-adjustable hemostatic clip comprising:
a first clip arm having a first clip arm distal end, and a second clip arm having a second clip arm distal end, said second clip arm opposes and is connected to said first clip arm at a shared proximal end configured as an elastic normally-opened joint portion, each one of said first and second clip arms includes an outer clip arm member connected to an inner clip arm member having a tissue contacting surface, and configured with a gap between said inner clip arm member and said outer clip arm member, such that said inner clip arm member elastically deforms or/and shifts towards a respective one of said outer clip arm member when said first and second clip arms are closed against, and mutually apply compression and clamping forces to, a bodily organ or tissue; and a locking mechanism configured for locking said first clip arm distal end to said second clip arm distal end;

wherein a first one of said inner clip arm member is connected to a first one of said outer clip arm member, via at least one first arm joining portion, and includes both a distal end portion and a proximal end portion that freely extend from said at least one first arm joining portion.

2. The hemostatic clip of claim 1, wherein said at least one first arm joining portion has a single first arm joining portion, wherein both said distal end portion and said proximal end portion of said first inner clip arm member freely extend from said single first arm joining portion.

3. The hemostatic clip of claim 2, wherein at least one of said distal end portion and said proximal end portion of said first inner clip arm member extends along a length greater than 3 mm from said single first arm joining portion.

4. The hemostatic clip of claim 1, wherein said at least one first arm joining portion includes a proximal first arm joining portion and a distal first arm joining portion, wherein said distal end portion of said first inner clip arm member freely extends distally from said distal first arm joining portion, and said proximal end portion of said first inner clip arm member freely extends proximally from said proximal first arm joining portion.

5. The hemostatic clip of claim 4, wherein said distal end portion of said first inner clip arm member extends along a length greater than 1 mm, distally from said distal first arm joining portion, or/and said proximal end portion of said first inner clip arm member extends along a length greater than 0.5 mm, proximally from said proximal first arm joining portion.

6. The hemostatic clip of claim 1, wherein a second one of said inner clip arm member is connected to a second one of said outer clip arm member, via at least one second arm joining portion distanced differently from said shared proximal end of said first and second clip arms relative to said at least one first arm joining portion.

7. The hemostatic clip of claim 6, wherein said at least one second arm joining portion includes a distal-most second arm joining portion and a proximal-most second arm joining portion, wherein said at least one first arm joining portion is provided between said distal-most second arm joining portion and said proximal-most second arm joining portion.

8. The hemostatic clip of claim 7, wherein said second inner clip arm member extends in full between said distal-most second arm joining portion and said proximal-most second arm joining portion.

9. The hemostatic clip of claim 1, wherein said first inner clip arm member has an intermediate portion provided between said distal end portion and proximal end portion of said first inner clip arm member, wherein said first inner clip arm member is configured such that resistance to deformation or/and shift towards said first outer clip arm member is greater along said intermediate portion than along any of said distal end portion and said proximal end portion of said first inner clip arm member.

10. The hemostatic clip of claim 6, wherein said first inner clip arm member has a first intermediate portion provided between said distal end portion and proximal end portion of said first inner clip arm member, wherein said first inner clip arm member is configured such that resistance to deformation or/and shift towards said first outer clip arm member is greater along said first intermediate portion than along any of said distal end portion and said proximal end portion of said first inner clip arm member; and wherein said second inner clip arm member has a second intermediate portion provided between a distal end portion and a proximal end portion of said second inner clip arm member, wherein said second inner clip arm member is configured such that resistance to deformation or/and shift towards said second outer clip arm member is smaller along said second intermediate portion than along any of said distal end portion and said proximal end portion of said second inner clip arm member.

11. The hemostatic clip of claim 1, wherein said gap is sized for accommodating said inner clip arm member that conforms to said bodily organ or tissue and outwardly bends toward said respective outer clip arm member.

12. The hemostatic clip of claim 1, wherein said first inner clip arm member is configured to apply a pressure of up to about 150 gr/mm$^2$ to said bodily organ or tissue.

13. The hemostatic clip of claim 1, wherein said locking mechanism includes a hook with a hook flange, said hook extends from a hook leg portion originating from said distal first arm joining portion and extending distally across entire length of said distal end portion of said first inner clip arm member.

14. The hemostatic clip of claim 13, wherein said locking mechanism further includes a niche with a cam surface in a form of a distal extension of second clip arm distal to second inner clip arm member, wherein said hook flange is configured to slidably engage along and beyond said cam surface, then fasten to said niche, when said first and second clip arms shift from an opened clip configuration to a locked clip configuration.

15. The hemostatic clip of claim 14, wherein said hook leg portion is curved towards first inner clip arm member until a hook apex provided distally and adjacent to distal end portion, wherein said distal end portion of said first inner clip arm member is configured to flex towards said hook leg portion, when pressed against the bodily organ or a tissue towards engaging with second clip arm, thereby supporting a length of said hook leg portion up to a point located adjacently and proximally to said hook apex.

16. The hemostatic clip of claim 1, wherein said first and second clip arms, and said locking mechanism, are integrally structured.

17. The hemostatic clip of claim 1, further comprising an interconnecting mechanism configured for sequentially chaining lengthwise, one after another, a plurality of the hemostatic clip, wherein said shared proximal end includes a tail coupler connectable to a head coupler provided at said second clip arm distal end.

* * * * *